(12) United States Patent
Ghosh et al.

(10) Patent No.: US 11,028,096 B2
(45) Date of Patent: *Jun. 8, 2021

(54) TRICYCLIC P2-LIGAND CONTAINING POTENT HIV-PROTEASE INHIBITORS AGAINST HIV/AIDS

(71) Applicant: PURDUE RESEARCH FOUNDATION, West Lafayette, IN (US)

(72) Inventors: Arun K. Ghosh, West Lafayette, IN (US); Hiroaki Mitsuya, Kumamoto (JP); Prasanth Reddy Nyalapatla, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/348,558

(22) PCT Filed: Nov. 9, 2017

(86) PCT No.: PCT/US2017/060840
§ 371 (c)(1),
(2) Date: May 9, 2019

(87) PCT Pub. No.: WO2018/089621
PCT Pub. Date: May 17, 2018

(65) Prior Publication Data
US 2019/0359626 A1 Nov. 28, 2019

Related U.S. Application Data

(60) Provisional application No. 62/419,850, filed on Nov. 9, 2016.

(51) Int. Cl.
*C07D 493/06* (2006.01)
*C07D 311/78* (2006.01)

(52) U.S. Cl.
CPC .......... *C07D 493/06* (2013.01); *C07D 311/78* (2013.01)

(58) Field of Classification Search
CPC .............................. C07D 493/06; C07D 311/78
USPC .......................................................... 549/458
See application file for complete search history.

(56) References Cited

U.S. PATENT DOCUMENTS 9,670,225 B2 * 6/2017 Ghosh .................... A61P 43/00

FOREIGN PATENT DOCUMENTS

| JP | 52083436 | * | 7/1977 | ............. C07C 61/38 |
| JP | 55-24139 A | | 2/1980 | |
| JP | H08-48678 A | | 2/1996 | |
| JP | 2019-534332 A | | 11/2019 | |
| WO | WO-2012/031237 A1 | | 3/2012 | |
| WO | WO-2012/092188 A1 | | 7/2012 | |
| WO | WO-2015175994 A1 | * | 11/2015 | ............. A61P 43/00 |
| WO | WO2015175994 A1 | | 11/2015 | |
| WO | WO-2018089621 A1 | | 5/2018 | |

OTHER PUBLICATIONS

Naruto, Masanobu et al. (+)-11-Deoxy-13, 14-dihydro-13β, 11α-epoxymethano-12-isoprostaglandin F2α from aucubin (Year: 1978).*
PubChem-CID-11393413, (Oct. 26, 2006), 3 pgs.
"International Application Serial No. PCT/US2017/060840, International Search Report dated Jan. 25, 2018", 3 pgs.
"International Application Serial No. PCT/US2017/060840, Written Opinion dated Jan. 25, 2018", 6 pgs.
Agniswamy, et al., "Extreme multidrug resistant HIV-1 protease with 20 mutations is resistant to novel protease inhibitors with PT-pyrrolidinone or P2-tris-tetrahydrofuran", , J Med Chem. vol. 56(10), entire document, especially: p. 14, Figure 1, Inhibitor 3, (2013), 2036-2046.
Amano, et al., "GRL-0519, a Novel Oxatricyclic Ligand-Containing Nonpeptidic HIV-1 Protease inhibitor (PI), Potently Suppresses Replication of a Wide Spectrum of Multi-PI-Resistant HIV-1 Variants In Vitro", Antimicrobial Agents and Chemotherapy. vol. 57(5), entire document, especially: p. 2037, Figure 1, GRL-0529, (2013), 2036-2046.
Ghosh, et al., "Highly Potent HIV-1 Protease inhibitors with Novel Tricyclic P2-ligands: Design, Synthesis, and Protein-ligand X-Ray Studies", J Med Chem. vol. 56(17), entire document, especially: p. 18, Figure 1, protease inhibitor 1, (2013), 6792-6802.
Zhang, et al., "Novel P2 tris-tetrahydrofuran group in antiviral compound 1 (GRL-0519) fills the S2 binding pocket of selected mutants of HIV-1 protease", J Med Chem. vol. 56(3), entire document, especially: p. 13, Figure 1, Inhibitor 1, GRL-0519, (2013), 1074-1083.
"European Application Serial No. 17869625.8, Extended European Search Report dated Mar. 26, 2020", 10 pgs.
"European Application Serial No. 17869625.8, Response filed Dec. 16, 2019 to Communication Pursuant to Rules 161(1) and 162 EPC filed Dec. 16, 2019", 14 pgs.
Birch, A. J., et al.,"1027. Aucubin", *Journal of the Chemical Society*, (Jan. 1, 1961), 5194-5198.
"International Application Serial No. PCT/US2017/060840, International Preliminary Report on Patentability dated May 23, 2019", 8 pgs.

* cited by examiner

*Primary Examiner* — Rita J Desai
(74) *Attorney, Agent, or Firm* — Schwegman Lundberg & Woessner, P.A.

(57) ABSTRACT

Various embodiments relate to a compound of the formula (I) and (II), wherein X, $X^1$, $X^2$, $X^3$, and $R^1$-$R^4$ are defined herein, as well as pharmaceutical compositions comprising compounds of the formula (I) and/or (II) and methods of treating an HIV infection comprising administering a therapeutically effective amount of one or more compounds of formula (I) and/or (II), or a pharmaceutical composition comprising compounds of the formula (I) and/or (II), to a patient in need thereof.

16 Claims, No Drawings

TRICYCLIC P2-LIGAND CONTAINING POTENT HIV-PROTEASE INHIBITORS AGAINST HIV/AIDS

CROSS-REFERENCE TO RELATED APPLICATIONS

This application is a U.S. National Stage Filing under 35 U.S.C. § 371 from International Application No. PCT/US2017/060840, filed Nov. 9, 2017, and published as WO 2018/089621 A1 on May 17, 2018, which claims the benefit of U.S. Provisional Application Ser. No. 62/419,850, filed Nov. 9, 2016, the entirety of which applications are incorporated by reference as if fully set forth herein.

STATEMENT OF GOVERNMENT SUPPORT

This invention was made with government support under grant GM053386 awarded by the National Institutes of Health. The government has certain rights in the invention.

BACKGROUND OF THE INVENTION

The AIDS epidemic is one of the most challenging problems in medicine in the 21st century. Among many strategies to combat this disease, highly active antiretroviral therapy (HAART) with HIV protease inhibitors (PIs) in combination with reverse transcriptase inhibitors (RTIs) continues to be the first line treatment for control of HIV infection. Although such combination therapy has improved quality of life, enhanced HIV management, and halted the progression of the disease, there remain many challenges to treating this devastating disease, including decreasing both the toxicity and complexity of these treatment regimens. In addition, there is a growing population of patients that is developing multi-drug resistant strains of HIV. And there is ample evidence that these strains can be further transmitted.

Even though HAART has had a major impact on the AIDS epidemic in industrially advanced nations, it has not achieved the eradication of human immunodeficiency virus type 1 (HIV 1), in part due to the viral reservoirs remaining in blood and infected tissues. The limitation of antiviral therapy of AIDS is also exacerbated by complicated regimens, the development of drug-resistant HIV-1 variants, and a number of inherent adverse effects. Further, efforts to bring about the optimal benefits of HAART have met with a number of challenges, including (i) drug-related toxicities; (ii) partial restoration of immunologic functions once individuals developed AIDS; (iii) development of various cancers as a consequence of survival prolongation; (iv) flameup of inflammation in individuals receiving HAART or immune re-construction syndrome (IRS); and (v) increased cost of antiviral therapy. Such limitations of HAART are exacerbated by the development of drug-resistant HIV-1 variant.

There is presently a paucity of antiretroviral drugs or agents that are not only substantially specific for HIV-1, but also devoid of toxicity or side effects in the therapy of AIDS.

DETAILED DESCRIPTION OF THE INVENTION

While the disclosed subject matter will be described in conjunction with the enumerated claims, it will be understood that the exemplified subject matter is not intended to limit the claims to the disclosed subject matter.

Various embodiments are directed to a compound of the formula (I):

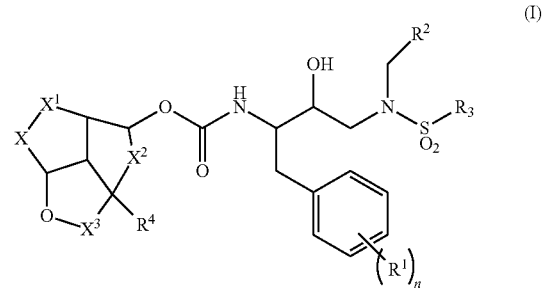

or a pharmaceutically acceptable salt, polymorph, prodrug, solvate or clathrate thereof, wherein: n is an integer from 0 to 3; X is $(-CHR^5-)_m$ or $-O-$, wherein m is 1 or 2 and each $R^5$ is, independently H, alkyl or alkoxy; $X^1$, $X^2$, and $X^3$ are each, independently, $(-CHR^5-)_m$; $R^1$ is alkyl, alkoxy, aryl, heterocyclyl, halo, hydroxy or amino; $R^2$ is alkyl; $R^3$ is aryl, benzthiazole, benzoxazole, benzofuranyl or indolyl; and $R^4$ is H, alkyl or alkoxy. In some examples, n is 0. In addition, (i) $X^1$ can be $(-CHR^5-)_m$, with m being 2, and $X^2$ and $X^3$ can each be $(-CHR^5-)_m$, with m being 1 and each $R^5$ being the same or different and as defined herein; or (ii) $X^1$ and $X^2$ can be $(-CHR^5-)_m$, with m being 1, and $X^3$ can be $(-CHR^5-)_m$, with m being 2 and each $R^5$ being the same or different and as defined herein. In either instance (i) or (ii), X can be O. In addition, either instance (i) or (ii), X can be $(-CHR^5-)_m$, wherein m is 1 and $R^5$ is as defined herein (e.g., H). In any of the foregoing examples, $R^4$ can be H or alkoxy.

Various other embodiments are directed to a compound of the formula (Ia)-(Ic):

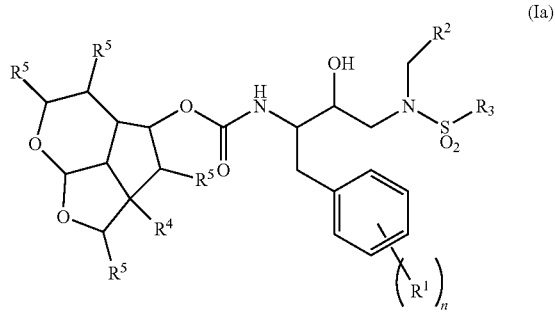

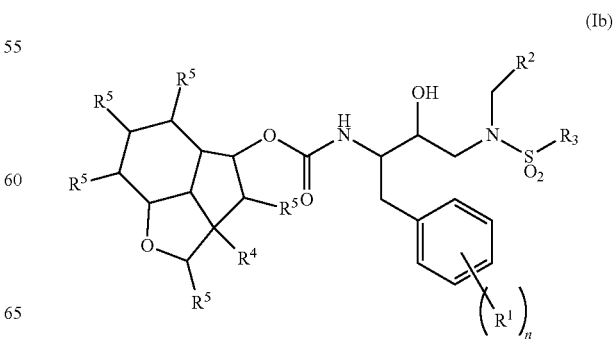

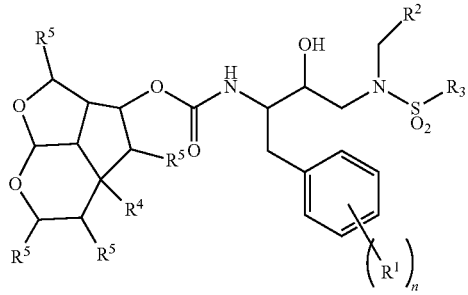
(Ic)
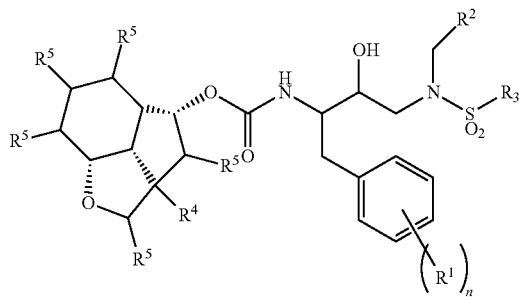
or a pharmaceutically acceptable salt, polymorph, prodrug, solvate or clathrate thereof, wherein n, $R^1$, $R^2$, $R^3$, $R^4$ and $R^5$ are as defined herein and wherein each $R^5$ can be the same or different.
All diastereomers of the compounds of the formula (I) and (Ia)-(Ic) are contemplated herein, including:
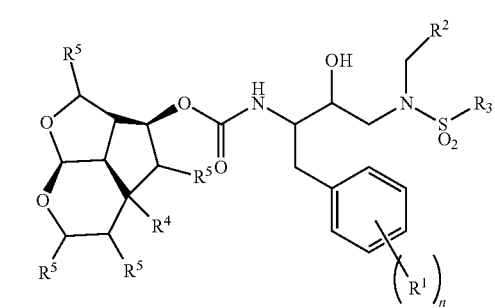
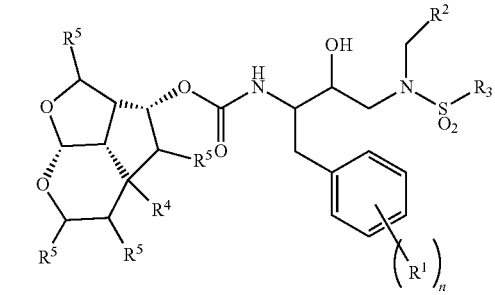
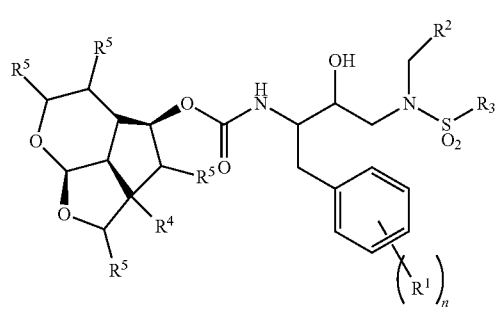
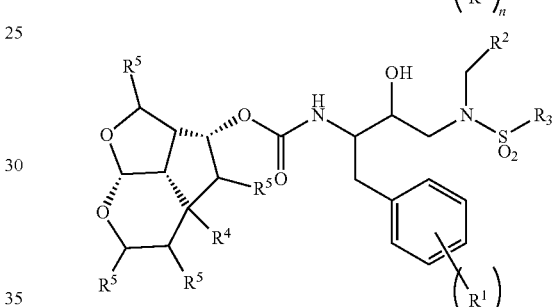
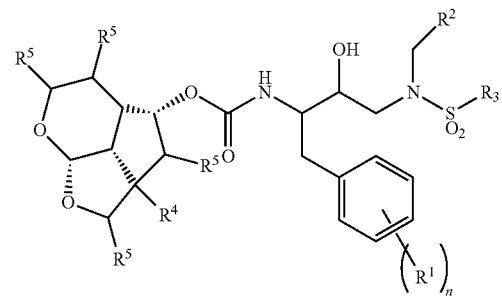
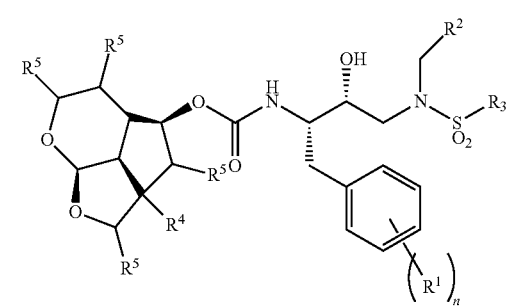
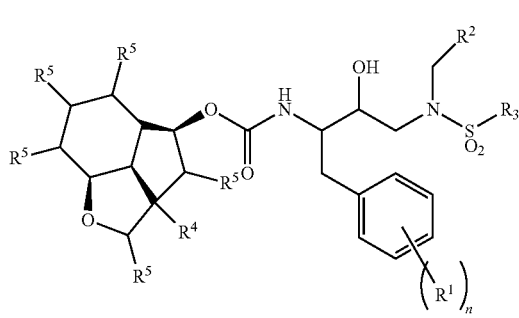
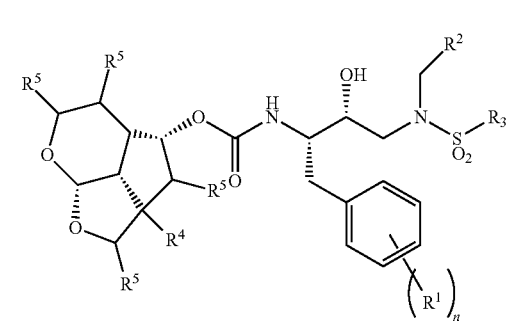

-continued

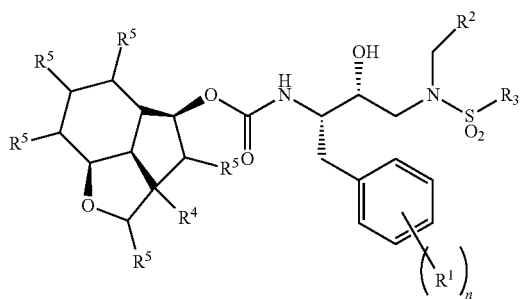

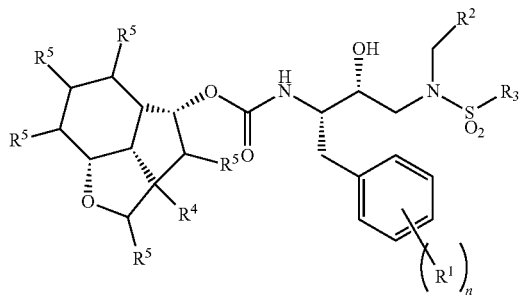

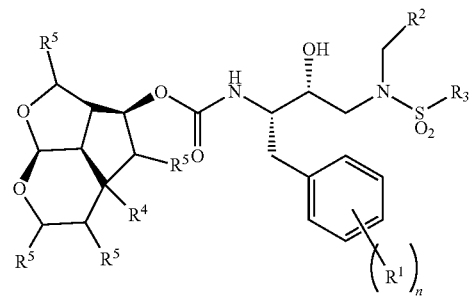

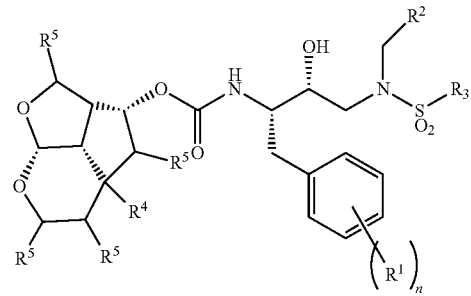

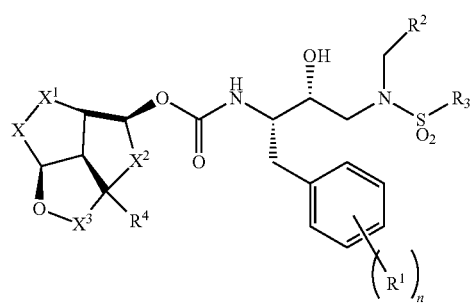

-continued

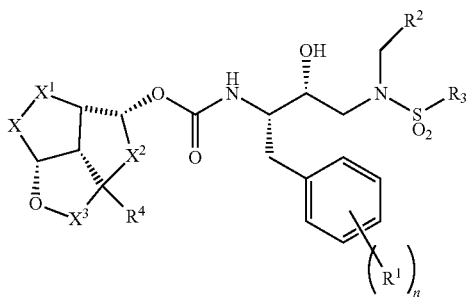

or a pharmaceutically acceptable salt, polymorph, prodrug, solvate or clathrate thereof, wherein n, $R^1$, $R^2$, $R^3$, and $R^4$. In addition, (i) $X^1$ can be $(-CHR^5-)_m$, with m being 2, and $X^2$ and $X^3$ can each be $(-CHR^5-)_m$, with m being 1 and each $R^5$ being the same or different and as defined herein; or (ii) $X^1$ and $X^2$ can be $(-CHR^5-)_m$, with m being 1, and $X^3$ can be $(-CHR^5-)_m$, with m being 2 and each $R^5$ being the same or different and as defined herein. In either instance (i) or (ii), X can be O. In addition, either instance (i) or (ii), X can be $(-CHR^5-)_m$, wherein m is 1 and $R^5$ is as defined herein (e.g., H). In any of the foregoing examples, $R^4$ can be H or alkoxy.

In any of the examples disclosed herein, $R^3$ can an unsubstituted or substituted aryl. $R^3$ can be, for example, phenyl. But $R^3$ can be substituted aryl. The substituted aryl groups represented by $R^3$ herein can be, for example, selected from the group consisting of:

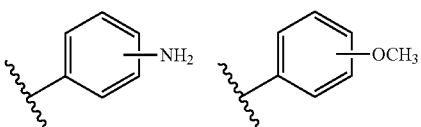

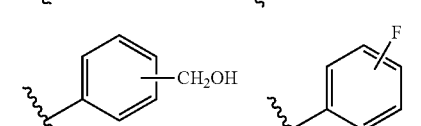

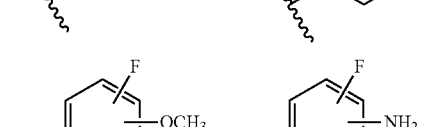

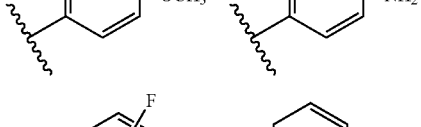

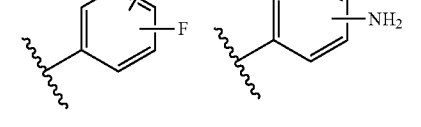

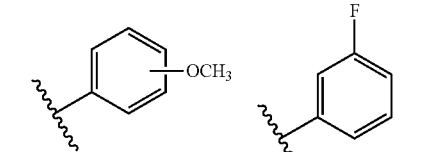

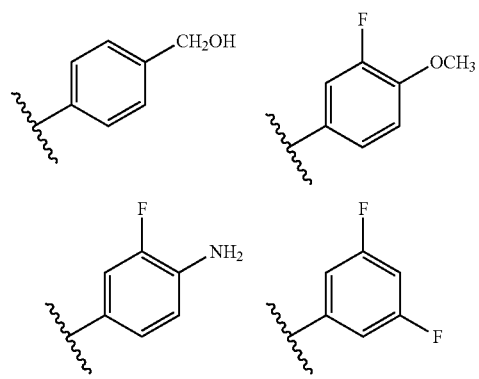

In any of the examples disclosed herein, $R^3$ is a benzthiazole or a benzoxazole:

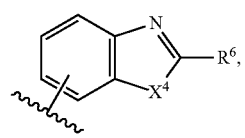

wherein $R^6$ is alkyl (e.g., $C_1$-$C_6$ alkyl), alkylamino (e.g., $C_1$-$C_6$ alkylamino), cycloalkylamino (e.g., $C_3$-$C_6$ cycloalkylamino), cycloalkyl heterocycloamino (e.g., $C_3$-$C_6$ cycloalkyl-$C_3$-$C_6$ heterocycloamino), heterocyclo cycloalkylamino (e.g., $C_3$-$C_6$ heterocyclo-$C_3$-$C_6$ cycloalkylamino) or heterocycloamino (e.g., $C_3$-$C_6$ heterocycloamino); and $X^4$ is S, O or $NR^7$, wherein $R^7$ is H, alklyl, cycloalkyl or alkylaryl. $X^1$ can be S or O.

Examples of the compounds of the formula (I) and (Ia)-(Ic) include, but are not limited to the compounds of formula 1-24:

1

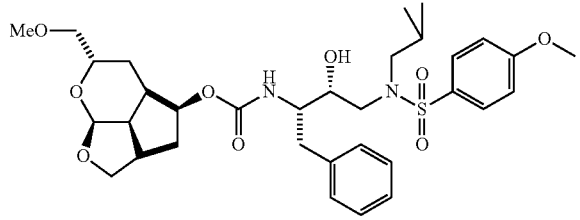

2

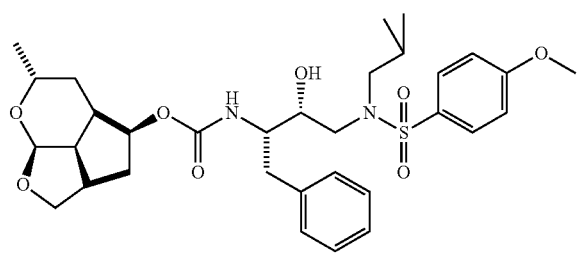

3

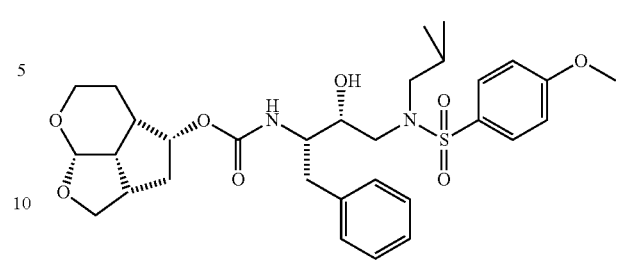

4

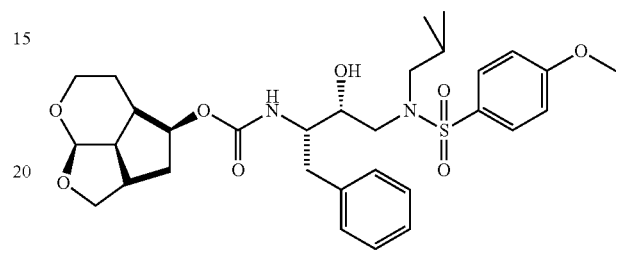

5

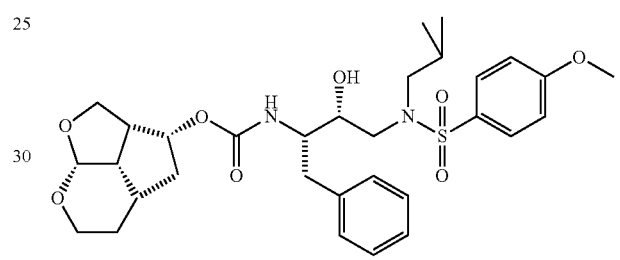

6

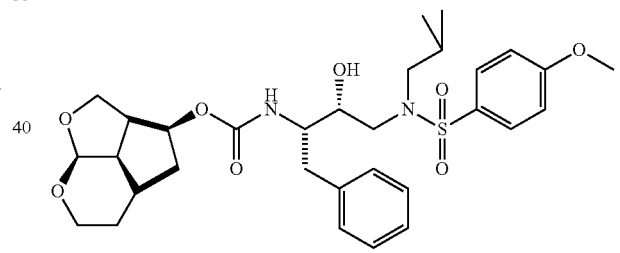

7

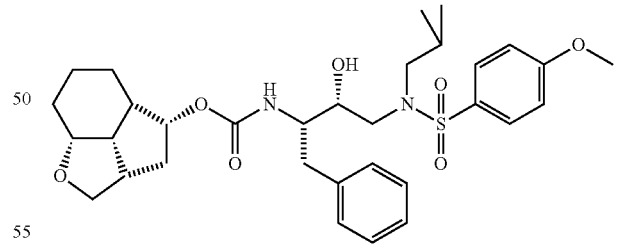

8

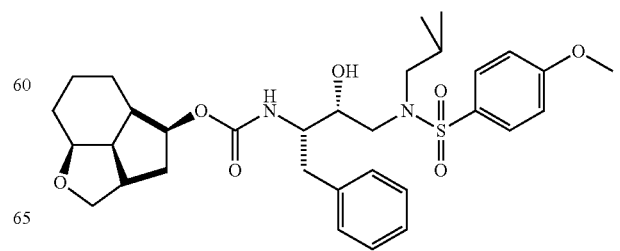

9
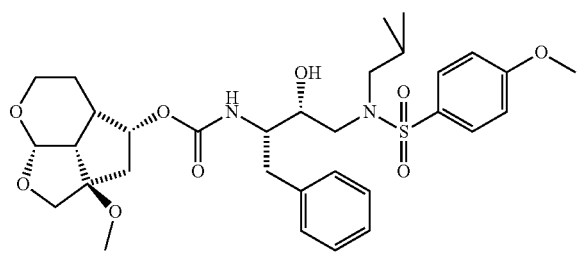
10
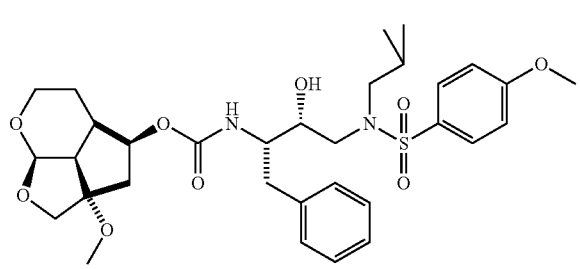
11
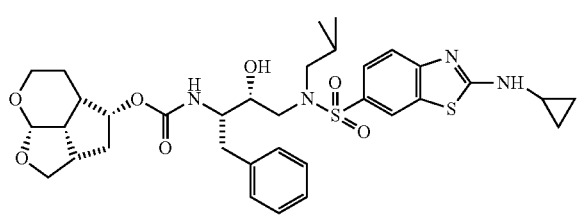
12
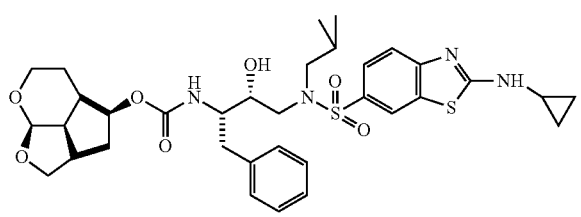
13
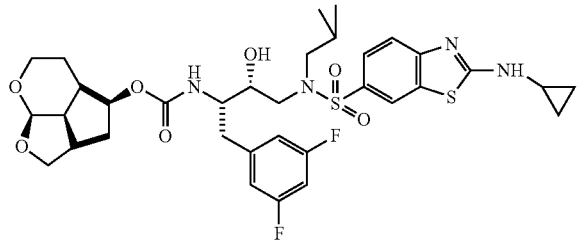
14
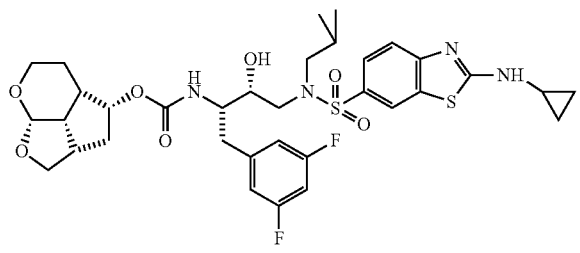
15
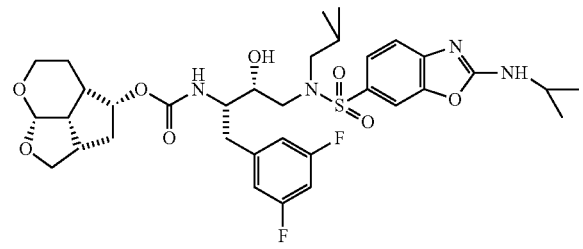
16
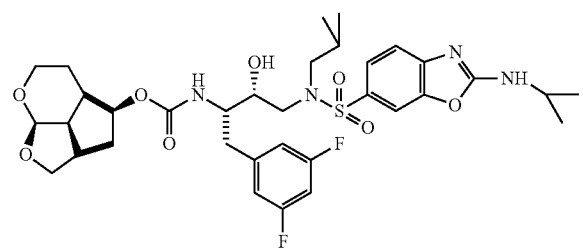
17
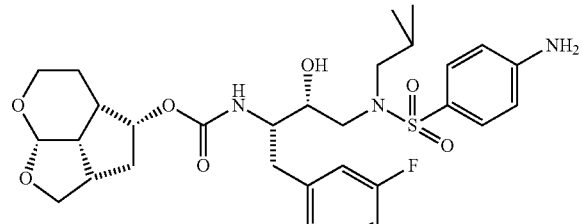
18
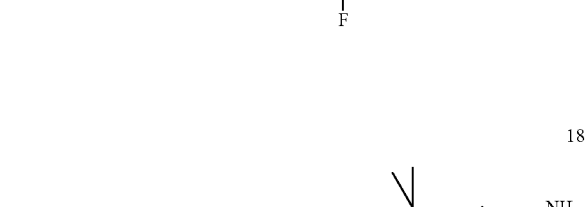
19
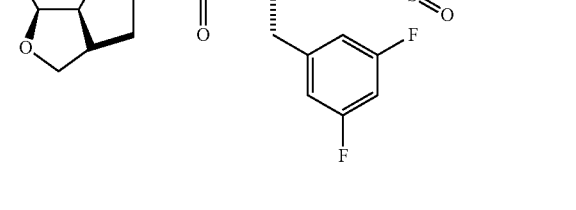
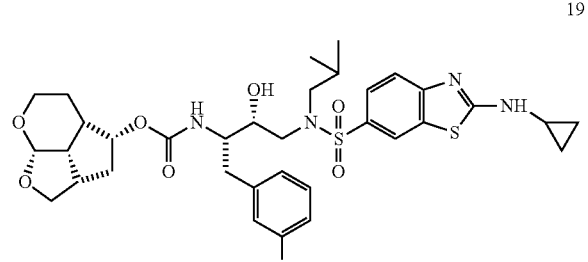

20

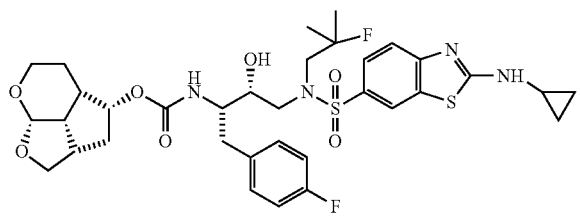

21

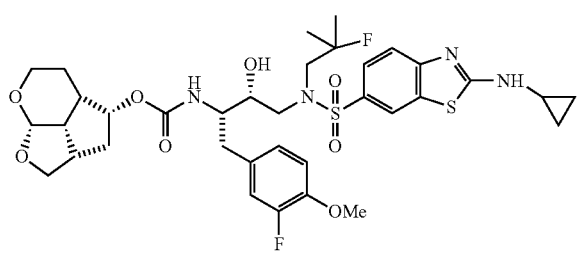

22

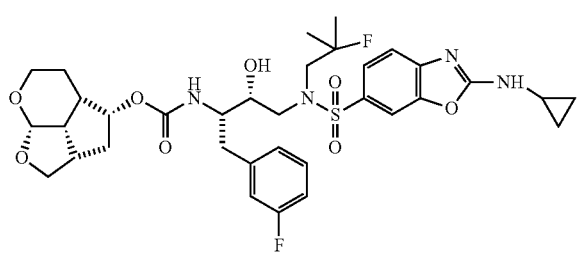

23

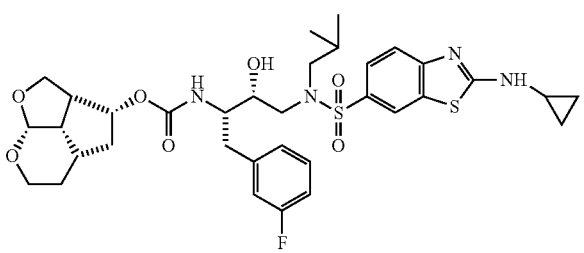

24

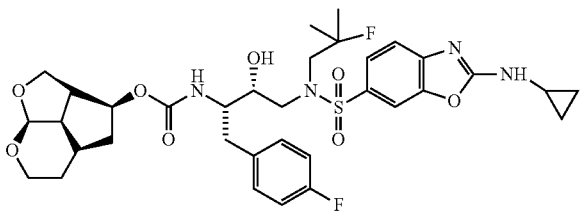

or a pharmaceutically acceptable salt, polymorph, prodrug, solvate or clathrate thereof.

Various other embodiments are directed to compounds of the formula (II), which can serve as, among other things, building blocks for the various compounds described herein:

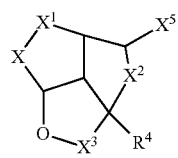

(II)

or a pharmaceutically acceptable salt, polymorph, prodrug, solvate or clathrate thereof, wherein X, $X^1$—$X^3$, and $R^4$ are defined herein and wherein $X^5$ is selected from the group consisting of hydroxy, alkoxy, amino, C(O)R, C(O)OR, OC(O)OR, C(O)N(R)$_2$, OC(O)N(R)$_2$, C(S)N(R)$_2$, (CH$_2$)$_{0-2}$O(R)C(O)R, (CH$_2$)$_{0-2}$N(R)C(O)R, (CH$_2$)$_{0-2}$O(R)C(O)OR, (CH$_2$)$_{0-2}$O(R)C(O)OR or (CH$_2$)$_{0-2}$N(R)N(R)$_2$, wherein each R can be, independently, hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or two R groups bonded to a nitrogen atom or to adjacent nitrogen atoms can together with the nitrogen atom or atoms form a heterocyclyl. In addition, (i) $X^1$ can be (—CHR$^5$—)$_m$, with m being 2, and $X^2$ and $X^3$ can each be (—CHR$^5$—)$_m$, with m being 1 and each R$^5$ being the same or different and as defined herein; or (ii) $X^1$ and $X^2$ can be (—CHR$^5$—)$_m$, with m being 1, and $X^3$ can be (—CHR$^5$—)$_m$, with m being 2 and each R$^5$ being the same or different and as defined herein. In either instance (i) or (ii), X can be O. In addition, either instance (i) or (ii), X can be (—CHR$^5$—)$_m$, wherein m is 1 and R$^5$ is as defined herein (e.g., H). In any of the foregoing examples, $R^4$ can be H or alkoxy.

Various other embodiments are directed to compounds of the formula (IIa-IIc):

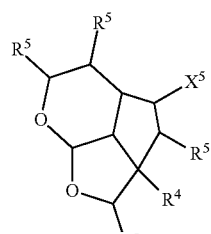

(IIa)

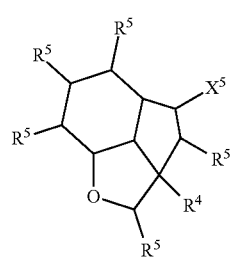

(IIb)

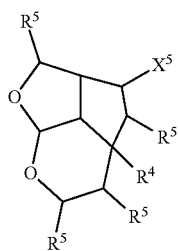

(IIc)

wherein $R^4$, $R^5$ and $X^5$ are defined herein.

All diastereomers of the compounds of the formula (II) and (IIa)-(IIc) are contemplated herein, including compounds of the formula:

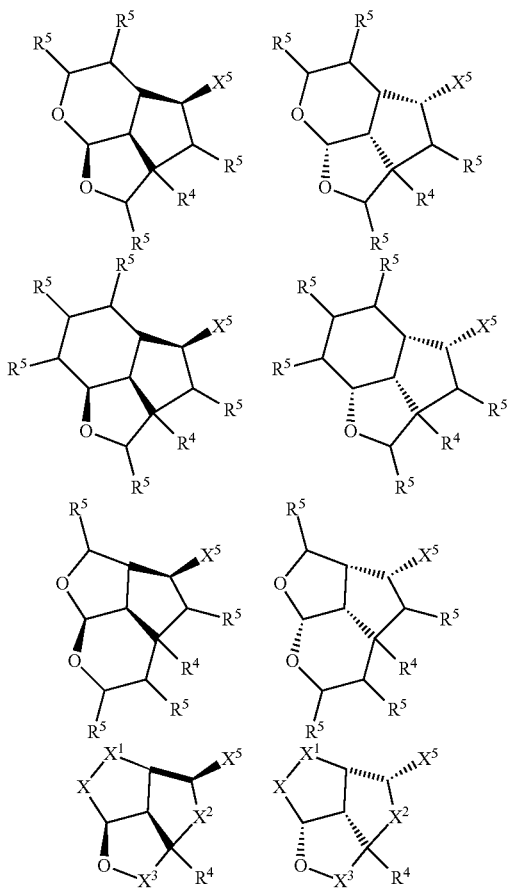

wherein X, $X^1$-$X^3$, $R^4$, and $X^5$ are as defined herein. In addition, (i) $X^1$ can be (—$CHR^5$—)$_m$, with m being 2, and $X^2$ and $X^3$ can each be (—$CHR^5$—)$_m$, with m being 1 and each $R^5$ being the same or different and as defined herein: or (ii) $X^1$ and $X^2$ can be (—$CHR^5$—)$_m$, with m being 1, and $X^3$ can be (—$CHR^5$—)$_m$, with m being 2 and each $R^5$ being the same or different and as defined herein. In either instance (i) or (ii), X can be O. In addition, either instance (i) or (ii), X can be (—$CHR^5$—)$_m$, wherein m is 1 and $R^5$ is as defined herein (e.g., H). In any of the foregoing examples, $R^4$ can be H or alkoxy.

Various embodiments also contemplate pharmaceutical compositions comprising one or more compounds of the various embodiments described herein (e.g. a compound of the formula (I), (Ia)-(Ic), (II), and 1-24) and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In some cases isotonic agents can be included in the pharmaceutical compositions, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal days; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the various embodiments described herein or an appropriate pharmaceutical composition thereof are effective, the compounds of the various embodiments described herein may be administered in an effective amount. The dosages as suitable for this invention may be a composition, a pharmaceutical composition or any other compositions described herein.

The dosage can be administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (nonlocal), composition is given via the digestive tract. Administration can be parenteral, where the desired effect is systemic, composition is given by other routes than the digestive tract.

Various embodiments contemplate compositions comprising a therapeutically effective amount of one or more compounds of the various embodiments described herein (e.g. a compound of the formula (I), (Ia)-(Ic), (II), and compounds 1-24). In some embodiments, the compositions are useful in a method for treating an HIV (e.g., HIV-1) infection or AIDS, the method comprising administering a therapeutically effective amount of one or more compounds of any preceding claim to a patient in need thereof. Various embodiments contemplate a compound of the formula (I), (Ia)-(Ic), (II) and compounds 1-24 for use as a medicament for treating a patient in need of relief from an HIV infection or AIDS.

The term "therapeutically effective amount" as used herein, refers to that amount of one or more compounds of the various embodiments described herein (e.g. a compound of the formula (I), (Ia)-(Ic), (II), and compounds 1-24) that elicits a biological or medicinal response in a tissue system, animal or human, that is being sought by a researcher, veterinarian, medical doctor or other clinician, which includes alleviation of the symptoms of the disease or disorder being treated. In some embodiments, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

In some embodiments, the compounds of the various embodiments described herein can have an HIV-1 protease inhibition constant ($K_i$) of from about 1 fM to about 200 nM (e.g., about 100 fM to about 200 nM, about 100 fM to about 100 pM, about 250 fM to about 100 pM, about 500 fM to about 5 pM, about 5 pM to about 100 pM, about 50 pM to about 250 pM, about 500 pM to about 100 nM or about 300 pM to about 75 nM).

In other embodiments, the compounds of the various embodiments described herein have an antiviral activity in vitro against a wild-type laboratory strain, HIV-1$_{LAI}$, with half-maximal inhibitory concentration ($IC_{50}$) of from about 1 fM to about 200 nM (e.g., about 100 fM to about 200 nM, about 100 fM to about 100 pM, about 250 fM to about 100 pM, about 500 fM to about 5 pM, from about 10 pM to about 50 nM, about 10 pM to about 500 pM, about 100 pM to about 750 pM, about 500 pM to about 1 nM or about 500 pM to about 50 nM).

In still other embodiments, the compounds of the various embodiments described herein have a darunavir-resistant HIV-1 variant (e.g., NL4-3R, DRV$_R$P20, DRV$_R$P30, and DRV$_R$P51) antiviral $IC_{50}$ of from about 200 fM to about 100 nM (e.g., from about 200 fM to about 600 fM, about 200 fM to about 50 pM, about 500 fM to about 500 pM, about 300 fM to about 1 pM). In yet other embodiments, the compounds of the various embodiments described herein have a darunavir-resistant HIV-1 variants (e.g., NL4-3R, DRV$_R$P20, DRV$_R$P30, and DRV$_R$P51) $IC_{50}$ of from about 50 pM to about 50 nM (e.g., from about 100 pM to about 50 nM or about 500 pM to about 10 nM). In still other embodiments, the compounds of the various embodiments described herein have a darunavir-resistant HIV-1 protease (e.g., NL4-3R, DRV$_R$P20, DRV$_R$P30, and DRV$_R$P51) anti- viral $IC_{50}$ of from about 1 nM to about 100 nM (e.g., from about 10 nM to about 75 nM or about nM to about 75 nM).

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "substituted" or "substituent" as used herein refers to a group that can be or is substituted onto a molecule or onto another group (e.g., on an aryl or an alkyl group). Examples of substituents include, but are not limited to, a halogen (e.g., F, Cl, Br, and I), OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, —(CH$_2$)$_{0-2}$P(O)(OR)$_2$, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)C(O)OR, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein each R can be, independently, hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or two R groups bonded to a nitrogen atom or to adjacent nitrogen atoms can together with the nitrogen atom or atoms form a heterocyclyl, which can be mono- or independently multi-substituted.

The term "alkyl" as used herein refers to substituted or unsubstituted straight chain and branched alkyl groups and cycloalkyl groups having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "cycloalkylalkyl" as used herein refers to substituted or unsubstituted alkyl groups as defined herein in which a hydrogen or carbon bond of an alkyl group as defined herein is replaced with a bond to a cycloalkyl group as defined herein. Representative cycloalkylalkyl groups include, but are not limited to, cyclopentylalkyl.

The term "alkylcycloalkyl" as used herein refers to substituted or unsubstituted cycloalkyl groups as defined herein in which a hydrogen of a cycloalkyl group as defined herein is replaced with a bond to an alkyl group as defined herein. Representative alkylcycloalkyl groups include, but are not limited to, alkylcyclopropyl.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "heterocyclylcarbonyl" is an example of an acyl group that is bonded to a substituted or unsubstituted heterocyclyl group, as the term "heterocyclyl" is defined herein. An example of a heterocyclylcarbonyl group is a prolyl group, wherein the prolyl group can be a D- or an L-prolyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" or "heterocyclo" as used herein refers to substituted or unsubstituted aromatic and non-aromatic ring compounds containing 3 or more ring members, of which, one or more (e.g., 1, 2 or 3) is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$), 3 to 5 carbon atoms ($C_3$-$C_5$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups. Examples of indolinonyl groups include groups having the general formula:

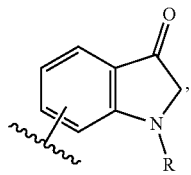

wherein R is as defined herein.
Examples of isoindolinonyl groups include groups having the general formula:

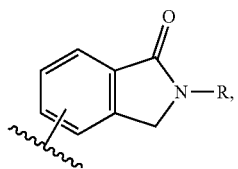

wherein R is as defined herein.
Examples of benzoxazolinyl groups include groups having the general formula:

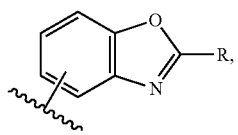

wherein R is as defined herein.
Examples of benzthiazolinyl groups include groups having the general formula:

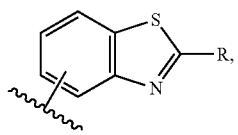

wherein R is as defined herein.
In some embodiments, the group R in benzoxazolinyl and benzthiazolinyl groups is an $N(R)_2$ group. In some embodiments, each R is hydrogen or alkyl, wherein the alkyl group is substituted or unsubstituted. In some embodiments, the alkyl group is substituted with a heterocyclyl group (e.g., with a pyrrolidinyl group).

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heterocyclylalkoxy" as used herein refers to alkyl groups as defined herein in which a hydrogen or carbon bond of an alkyl group as defined herein is replaced with a bond to a heterocyclyl group as defined herein and the alkyl group is attached to an oxygen. Representative heterocyclylalkoxy groups include, but are not limited to, —O—$(CH_2)_q$ heterocyclyl, wherein q is an integer from 1 to 5. In some embodiments, heterocyclylalkoxy groups include —O—$(CH_2)_q$morpholinyl such as —O—$CH_2CH_2$-morpholine.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to R—$NH_2$, for example, alkylamines, arylamines, alkylarylamines; $R_2NH$ wherein R is defined herein, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —$NH_2$, —NHR, —$NR_2$, —$NR_3^+$, wherein each R is defined herein, and protonated forms of each, except for —$NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

An example of a "alkylamino" is —NH-alkyl and —N(alkyl)$_2$.

An example of a "cycloalkylamino" group is —NH-cycloalkyl and —N(cycloalkyl)$_2$.

An example of a "cycloalkyl heterocycloamino" group is —NH-(heterocyclo cycloalkyl), wherein the heterocyclo group is attached to the nitrogen and the cycloalkyl group is attached to the heterocyclo group.

An example of a "heterocyclo cycloamino" group is —NH-(cycloalkyl heterocycle), wherein the cycloalkyl group is attached to the nitrogen and the heterocyclo group is attached to the cycloalkyl group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —CF(CH₃)₂ and the like.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

EXAMPLES

The present invention can be better understood by reference to the following examples which are offered by way of illustration. The present invention is not limited to the examples given herein.

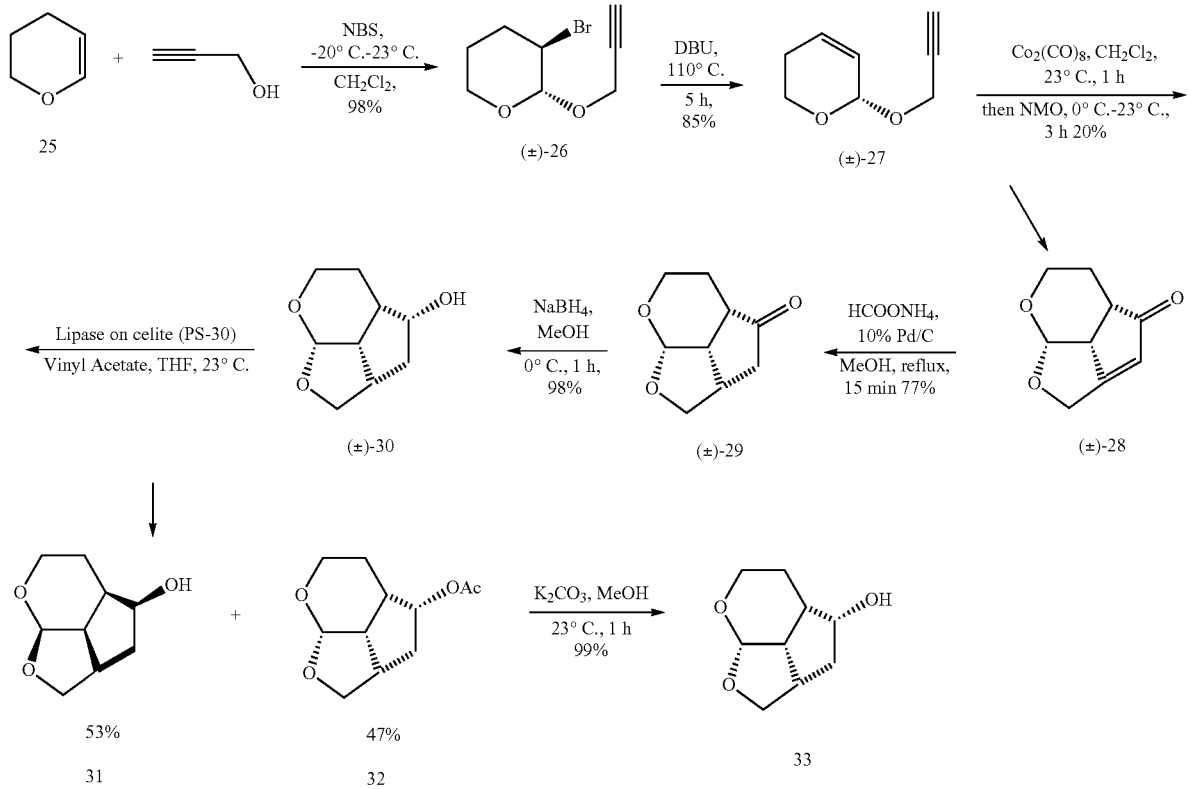

Scheme 1: Synthesis of tricyclic Ligands:

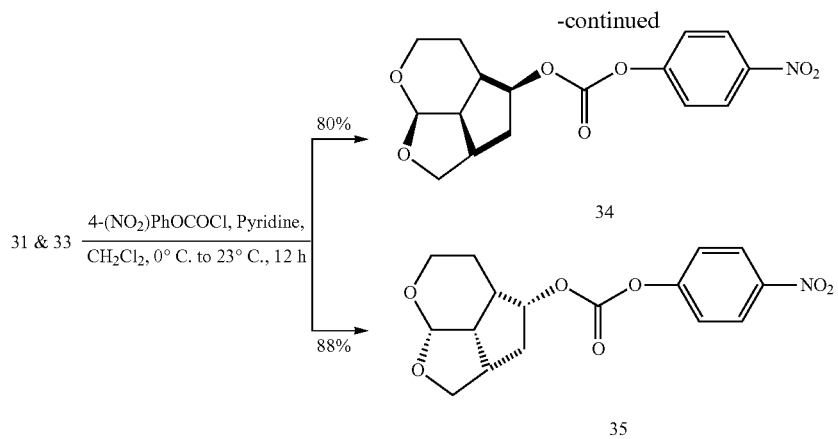

Experimental Procedure trans-3-Bromo-2-(prop-2-yn-1-yloxy)tetrahydro-2H-pyran (26)

To a stirred solution of olefin 25 (5.39 mL, 59.44 mmol) and propargyl alcohol (10.4 mL, 178.32 mmol) in dichloromethane (10 mL) was added NBS (11.63 g, 65.38 mmol) in small portions over 0.5 h at −20° C. under argon atmosphere. The reaction mixture was stirred at −20° C. for 2 h and further 15 h at 23° C. After this period, the reaction mixture was quenched by the addition of water and extracted with dichloromethane. The extracts were washed with Saturated aqueous $NaHSO_3$ solution, aqueous $K_2CO_3$ solution, water, dried ($Na_2SO_4$) and concentrated under reduced pressure. The crude product was purified by silica gel column chromatography (15% $Et_2O$ in hexane) to afford 26 (12.7 g, 98%).

$^1$H NMR (400 MHz, $CDCl_3$) δ: 4.85 (d, J=3.9 Hz, 1H), 4.30 (dd, J=4.8, 2.4 Hz, 2H), 4.01 (dt, J=5.7, 4.0 Hz, 1H), 3.89 (ddd, J=11.7, 8.6, 3.5 Hz, 1H), 3.65-3.58 (m, 1H), 2.46 (t, J=2.4 Hz, 1H), 2.44-2.34 (m, 1H), 1.96 (dddd, J=18.6, 10.3, 7.6, 4.4 Hz, 2H), 1.52 (dtd, J=15.1, 6.0, 3.1 Hz, 1H).

6-(Prop-2-yn-1-yloxy)-3,6-dihydro-2H-pyran (27)

A mixture of 26 (10 g, 45.65 mmol) and DBU (34 mL, 228.25 mmol) was stirred at 110° C. for 5 h under argon atmosphere. After this period, the reaction mixture was cooled, 100 mL of anhydrous ether was added and stirred for 1 h. The mixture was filtered through a plug of Celite, washed with ether and concentrated under reduced pressure by using cold bath. The crude product was purified by silica gel column chromatography (15% $Et_2O$ in pentane) to afford 27 (5.36 g, 85%) as a volatile liquid.

$^1$H NMR (400 MHz, $CDCl_3$) δ: 6.09-6.03 (m, 1H), 5.73 (dtd, J=10.1, 2.8, 1.3 Hz, 1H), 5.09 (s, 1H), 4.27 (d, J=2.4 Hz, 2H), 3.88 (td, J=11.4, 3.6 Hz, 1H), 3.72 (ddt, J=11.1, 6.1, 1.1 Hz, 1H), 2.41 (t, J=2.4 Hz, 1H), 2.37-2.25 (m, 1H), 1.94-1.85 (m, 1H).

2a$^1$,5,6,7a-Tetrahydro-2H-1,7-dioxacyclopenta[cd]inden-4(4aH)-one (28)

To a stirred solution of 27 (1.57 g, 11.4 mmol) in dichloromethane (40 mL) was added $Co_2(CO)_8$ (4.3 g, 12.5 mmol) at 23° C. under argon atmosphere. The reaction mixture was stirred at 23° C. for 1 h. After this period, to the above mixture was added NMO (8 g, 68.4 mmol) at 0° C. and the reaction mixture was stirred for 3 h at 23° C. The mixture was filtered through a plug of Celite, washed with dichloromethane and concentrated under reduced pressure. The crude product was purified by silica gel column chromatography (40% EtOAc in Hexane) to afford 28 (380 mg, 20%).

$^1$H NMR (400 MHz, $CDCl_3$) δ: 6.04 (s, 1H), 5.32 (d, J=5.2 Hz, 1H), 4.70 (qt, J=15.9, 1.7 Hz, 2H), 3.61 (ddd, J=12.1, 5.3, 4.0 Hz, 1H), 3.39 (ddd, J=12.0, 9.2, 2.8 Hz, 1H), 3.18 (dtt, J=6.9, 4.8, 2.0 Hz, 1H), 2.92 (dt, J=9.3, 6.5 Hz, 1H), 1.94-1.84 (m, 1H), 1.46 (dddd, J=14.3, 9.2, 6.6, 3.9 Hz, 1H).

$^{13}$C NMR (100 MHz, $CDCl_3$) δ: 211.8, 180.2, 123.9, 97.7, 66.2, 61.3, 47.3, 44.1, 24.4.

Hexahydro-2H-1,7-dioxacyclopenta[cd]inden-4(4aH)-one (29)

To a stirred solution of 28 (165 mg, 0.99 mmol) in MeOH (5 mL) were added $HCOONH_4$ (626 mg, 9.93 mmol) and 10% Pd/C (25 mg) at 23° C. under argon atmosphere. The reaction mixture was refluxed for 15 min. After this period, the reaction mixture was cooled to 23° C. and filtered through a plug of Celite. MeOH was removed under reduced pressure. To the crude residue was added chloroform to precipitate out of the excess $HCOONH_4$, filtered and concentrated under reduced pressure. The crude product was purified by silica gel column chromatography (45% EtOAc in Hexane) to afford 29 (128 mg, 77%).

$^1$H NMR (400 MHz, $CDCl_3$) δ: 5.03 (d, J=4.8 Hz, 1H), 3.94 (dd, J=9.2, 6.2 Hz, 1H), 3.76-3.71 (m, 1H), 3.62-3.52 (m, 2H), 2.96-2.82 (m, 2H), 2.67 (dd, J=19.0, 9.8 Hz, 1H), 2.53-2.45 (m, 1H), 2.18 (dd, J=18.9, 3.8 Hz, 1H), 2.10-2.02 (m, 1H), 1.72 (ddt, J=13.5, 10.7, 6.5 Hz, 1H).

$^{13}$C NMR (100 MHz, $CDCl_3$) δ: 217.1, 100.8, 73.1, 58.7, 43.6, 42.6, 41.2, 35.4, 21.1.

Octahydro-2H-1,7-dioxacyclopenta[cd]inden-4-ol (30)

To a stirred solution of 29 (88 mg, 0.52 mmol) in MeOH (5 mL) was added $NaBH_4$ (24 mg, 0.63 mmol) at 0° C. under argon atmosphere. The reaction mixture was stirred at 0° C. for 1 h. After this period the reaction mixture was quenched by the addition of Saturated aqueous $NH_4Cl$ and the layers were separated. The aqueous layer was extracted with EtOAc, combined organic extracts were dried over $Na_2SO_4$ and concentrated under reduced pressure. The crude product was purified by silica gel column chromatography (50% EtOAc in hexane) to give 30 (87 mg, 98%).

$^1$H NMR (400 MHz, CDCl$_3$) δ: 5.06 (d, J=5.4 Hz, 1H), 4.14-4.06 (m, 1H), 4.00 (dt, J=11.8, 6.8 Hz, 1H), 3.89-3.81 (m, 1H), 3.71 (dd, J=9.3, 4.4 Hz, 1H), 3.51 (dt, J=11.5, 5.6 Hz, 1H), 3.37 (d, J=9.1 Hz, 1H), 2.70 (ddq, J=12.6, 8.1, 4.1 Hz, 1H), 2.50 (td, J=9.6, 5.4 Hz, 1H), 2.19 (dq, J=11.2, 5.7 Hz, 1H), 1.93 (ddd, J=13.6, 8.4, 5.2 Hz, 1H), 1.78 (dt, J=7.8, 4.3 Hz, 2H), 1.68 (dt, J=13.7, 3.4 Hz, 1H).

$^{13}$C NMR (100 MHz, CDCl$_3$) δ: 101.0, 77.4, 71.8, 59.9, 41.8, 40.8, 40.4, 38.0, 21.2.

(2aR,2a$^1$R,4S,4aR,7aR)-Octahydro-2H-1,7-dioxacyclopenta[cd]inden-4-ol (31) and (2aS,2a$^1$S,4R,4aS,7aS)-Octahydro-2H-1,7-dioxacyclopenta[cd]inden-4-yl acetate (32)

To a solution of alcohol 30 (60 mg, 0.35 mmol) in THF (5 mL) were added vinyl acetate (0.6 ml, 6.2 mmol) and Lipase PS-30 on celite (100 mg) at 23° C. under argon atmosphere. The reaction mixture was stirred for 6 h (50:50 by $^1$H-NMR). After this period, the reaction mixture was filtered through a plug of Celite and solvents were removed under reduced pressure. The crude product was purified via silica gel column chromatography (30% to 50% EtOAc in hexane) to yield alcohol 31 (32 mg, 53%) and acetate 32 (35 mg, 47%).

Alcohol 31: $^1$H NMR (400 MHz, CDCl$_3$) δ: 5.08 (d, J=5.2 Hz, 1H), 4.12 (s, 1H), 4.04 (dt, J=12.3, 7.0 Hz, 1H), 3.88 (t, J=8.8 Hz, 1H), 3.75 (dd, J=9.3, 4.1 Hz, 1H), 3.55 (dd, J=11.5, 5.7 Hz, 1H), 3.31 (d, J=8.5 Hz, 1H), 2.80-2.68 (m, 1H), 2.53 (td, J=9.5, 5.5 Hz, 1H), 2.21 (dq, J=10.1, 5.4 Hz, 1H), 1.96 (ddt, J=13.5, 8.4, 4.8 Hz, 1H), 1.84 (t, J=5.8 Hz, 2H), 1.73 (d, J=13.8 Hz, 1H).

$^{13}$C NMR (100 MHz, CDCl$_3$) δ: 101.1, 77.5, 71.9, 59.9, 41.8, 41.0, 40.8, 38.2, 21.2.

Acetate 32: $^1$H NMR (400 MHz, CDCl$_3$) δ: 5.22 (d, J=5.1 Hz, 1H), 5.10 (dt, J=8.7, 6.2 Hz, 1H), 4.01-3.89 (m, 2H), 3.70 (dd, J=8.6, 6.3 Hz, 1H), 3.41 (dt, J=11.5, 6.5 Hz, 1H), 2.65 (qt, J=7.8, 5.1 Hz, 1H), 2.54 (ddd, J=14.6, 11.8, 6.8 Hz, 2H), 2.15-2.06 (m, 1H), 2.03 (s, 3H), 1.66 (dt, J=12.8, 8.4 Hz, 1H), 1.58-1.51 (m, 2H).

$^{13}$C NMR (100 MHz, CDCl$_3$) δ: 170.7, 100.6, 78.7, 72.1, 60.6, 42.2, 39.4, 35.7, 34.6, 21.9, 21.1.

(2aS,2a$^1$S,4R,4aS,7aS)-Octahydro-2H-1,7-dioxacyclopenta[cd]inden-4-ol (33)

To a stirred solution of acetate 32 (32 mg, 0.15 mmol) in MeOH (3 mL) was added K$_2$CO$_3$ (31 mg, 0.23 mmol) at 23° C. under argon atmosphere. The reaction mixture was stirred at 23° C. for 1 h. After this period the reaction mixture was quenched by the addition of Saturated aqueous NH$_4$Cl and the layers were separated. The aqueous layer was extracted with EtOAc, combined organic extracts were dried over Na$_2$SO$_4$ and concentrated under reduced pressure. The crude product was purified by silica gel column chromatography (50% EtOAc in hexane) to afford 33 (26 mg, 99%).

$^1$H NMR (400 MHz, CDCl$_3$) δ: 5.09 (d, J=5.3 Hz, 1H), 4.16-4.09 (m, 1H), 4.09-4.00 (m, 1H), 3.91-3.84 (m, 1H), 3.75 (dd, J=9.4, 4.2 Hz, 1H), 3.56 (dt, J=11.4, 5.5 Hz, 1H), 2.75 (dtt, J=12.3, 8.2, 3.6 Hz, 1H), 2.53 (td, J=9.6, 5.4 Hz, 1H), 2.21 (dq, J=10.2, 5.5 Hz, 1H), 1.96 (ddd, J=13.6, 8.4, 5.1 Hz, 1H), 1.83 (q, J=8.8, 7.3 Hz, 2H), 1.73 (dt, J=13.8, 2.9 Hz, 1H).

$^{13}$C NMR (100 MHz, CDCl$_3$) δ: 101.1, 77.5, 71.9, 59.9, 41.8, 41.0, 40.8, 38.2, 21.2.

4-Nitrophenyl ((2aR,2a$^1$R,4S,4aR,7aR)-octahydro-2H-1,7-dioxacyclopenta[cd]inden-4-yl) carbonate (34)

To a stirred solution of alcohol 31 (30 mg, 0.18 mmol) in dichloromethane (4 mL) was added pyridine (57 μL, 0.7 mmol) at 23° C. under argon atmosphere and the reaction mixture was cooled to 0° C. followed by addition of 4-nitrophenyl chloroformate (53 mg, 0.26 mmol). The reaction mixture was warmed to 23° C. and stirred for 12 h. Upon, completion, solvents were removed under reduced pressure and crude product was purified by silica gel column chromatography (35% EtOAc in hexane) to give 34 (47 mg, 80%).

$^1$H NMR (400 MHz, CDCl$_3$) δ: 8.28 (d, J=9.2 Hz, 2H), 7.38 (d, J=9.2 Hz, 2H), 5.27 (d, J=5.4 Hz, 1H), 5.16 (dt, J=8.8, 6.4 Hz, 1H), 4.07-3.97 (m, 2H), 3.77 (dd, J=8.9, 6.1 Hz, 1H), 3.47 (dt, J=11.4, 6.4 Hz, 1H), 2.79-2.66 (m, 2H), 2.59 (ddd, J=10.7, 9.2, 5.5 Hz, 1H), 2.29 (ddd, J=13.7, 8.0, 6.3 Hz, 1H), 1.85 (dt, J=13.0, 8.3 Hz, 1H), 1.73-1.66 (m, 2H).

$^{13}$C NMR (100 MHz, CDCl$_3$) δ: 155.4, 152.1, 145.4, 125.4, 121.9, 100.6, 83.6, 72.0, 60.5, 41.9, 39.2, 35.9, 34.7, 21.8.

4-Nitrophenyl ((2aS,2a$^1$S,4R,4aS,7aS)-octahydro-2H-1,7-dioxacyclopenta[cd]inden-4-yl) carbonate (35)

The title compound (35) was obtained by following the procedure outlined for compound 34 (51 mg, 88% yield).

$^1$H NMR (400 MHz, CDCl$_3$) δ: 8.26 (d, J=9.0 Hz, 2H), 7.36 (d, J=9.0 Hz, 2H), 5.26 (d, J=5.4 Hz, 1H), 5.19-5.10 (m, 1H), 4.00 (ddd, J=16.4, 11.4, 6.6 Hz, 2H), 3.75 (dd, J=8.6, 6.3 Hz, 1H), 3.46 (dt, J=11.9, 6.4 Hz, 1H), 2.71 (tt, J=15.2, 7.9 Hz, 2H), 2.63-2.55 (m, 1H), 2.28 (dt, J=13.7, 7.2 Hz, 1H), 1.84 (dt, J=13.0, 8.3 Hz, 1H), 1.72-1.65 (m, 2H).

$^{13}$C NMR (100 MHz, CDCl$_3$) δ: 155.5, 152.1, 145.5, 125.4, 121.9, 100.5, 83.6, 72.0, 60.4, 41.9, 39.2, 35.9, 34.6, 21.8.

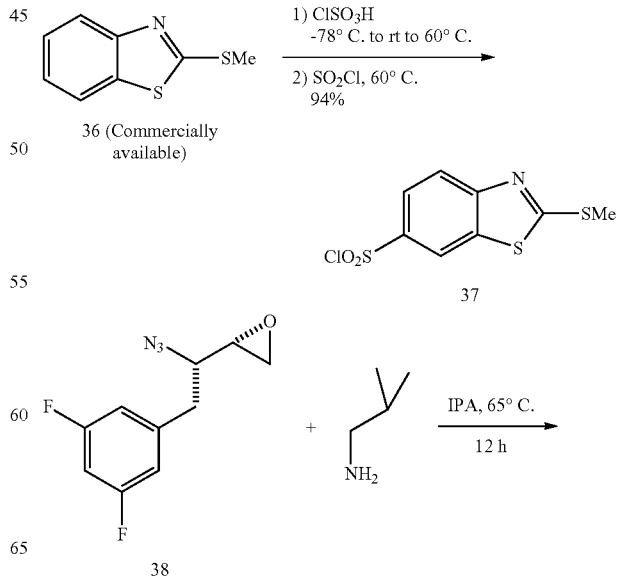

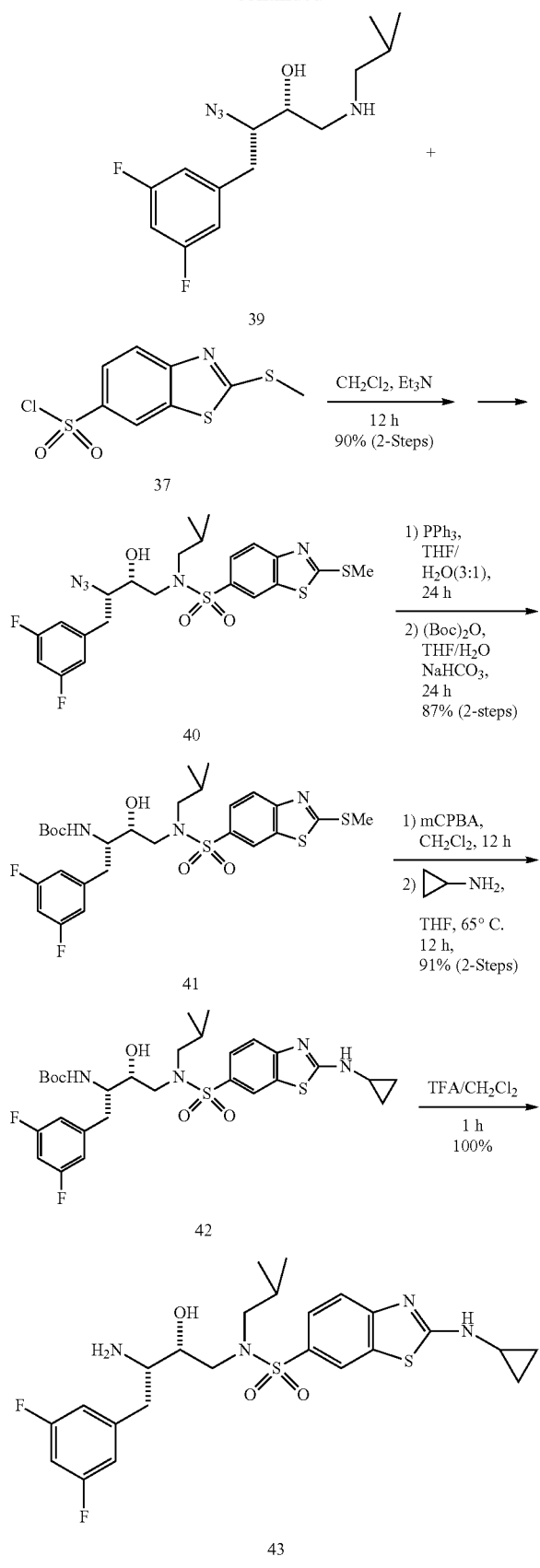

Experimental Procedure

2-(Methylthio)benzo[d]thiazole-6-sulfonyl chloride (37)

Chlorosulfonic acid (5.1 mL, 77.35 mmol) was added to 2-(Methylthio)benzothiazole (36) (2 g, 11 mmol) slowly (very exothermic) at −78° C. under argon atmosphere. The reaction mixture was warmed to 23° C. and stirred at 60° C. for 90 min. Again, the mixture was cooled to 23° C. before adding thionyl chloride (1.2 mL, 16.57 mmol). The reaction mixture was stirred at reflux for 1 h and cool to 23° C. EtOAc and water were added to the cooled mixture slowly until bubbles ceased. Two layers were separated, organic layer was concentrated, dried ($Na_2SO_4$) and purified by silica gel column chromatography to give 37 (2.9 g, 94% yield).

$^1$H NMR (500 MHz, $CDCl_3$) δ: 8.46 (d, J=1.5 Hz, 1H), 8.07 (dd, J=9.0, 2.0 Hz, 1H), 8.00 (d, J=9.0 Hz, 1H), 2.85 (s, 3H).

$^{13}$C NMR (125 MHz, $CDCl_3$) δ: 175.9, 157.4, 139.5, 136.0, 125.0, 122.1, 121.1, 16.3.

N-((2R,3S)-3-Azido-4-(3,5-difluorophenyl)-2-hydroxybutyl)-N-isobutyl-2-(methylthio)benzo[d]thiazole-6-sulfonamide (40)

Isobutylamine (0.27 mL, 2.66 mmol) was added to a stirred solution of 38 (200 mg, 0.89 mmol) in isopropanol at 23° C. under argon atmosphere. The reaction mixture was stirred at 65° C. for 12 h. After this period, isopropanol was removed under reduced pressure, to the crude product 39 in dichloromethane were added sulfonyl chloride 37 (248 mg, 0.89 mmol) and triethyl amine (0.37 mL, 2.66 mmol) at 23° C. under argon atmosphere. The reaction mixture was stirred at 23° C. for 12 h. Solvent was removed under reduced pressure and the crude product was purified by silica gel column chromatography (15% EtOAc in hexane) to give 40 (433 mg, 90% over two steps).

$^1$H NMR (500 MHz, $CDCl_3$) δ: 8.23-8.21 (m, 1H), 7.89 (d, J=8.6 Hz, 1H), 7.80-7.76 (m, 1H), 6.79 (d, J=6.2 Hz, 2H), 6.65 (t, J=8.9 Hz, 1H), 3.76 (d, J=17.6 Hz, 2H), 3.56 (ddd, J=9.5, 6.1, 3.7 Hz, 1H), 3.27-3.17 (m, 2H), 3.05 (ddd, J=21.8, 13.7, 5.8 Hz, 2H), 2.89 (dd, J=13.4, 6.8 Hz, 1H), 2.76 (s, 3H), 2.74-2.70 (m, 1H), 1.88-1.78 (m, 1H), 0.87 (d, J=6.6 Hz, 3H), 0.84 (d, J=6.6 Hz, 3H).

$^{13}$C NMR (100 MHz, $CDCl_3$) δ: 173.6, 164.4 (d, J=12.7 Hz), 161.9 (d, J=12.9 Hz), 156.1, 141.3 (t, J=9.1 Hz), 136.0, 133.7, 125.1, 121.9, 121.1, 112.6, 112.3, 102.6 (t, J=25.3 Hz), 71.9, 66.0, 59.1, 53.2, 36.6, 27.3, 20.2, 19.9, 16.1.

Tert-butyl((2S,3R)-1-(3,5-difluorophenyl)-3-hydroxy-4-((N-isobutyl-2-(methylthio)benzo[d]thiazole)-6-sulfonamido)butan-2-yl)carbamate (41)

Triphenylphosphine (160 mg, 0.61 mmol) was added to a stirred solution of 40 (275 mg, 0.5 mmol) in THF/$H_2O$ (3:1 ratio, 4 mL) at 23° C. The reaction mixture was stirred at 23° C. for 24 h. After this period, to the reaction mixture Boc anhydride (133 mg, 0.61 mmol) and Sodium bicarbonate (85 mg, 1 mmol) were added at 23° C. The reaction mixture was stirred at 23° C. for 20 h. The mixture was concentrated under reduced pressure and diluted with EtOAc. The reaction mixture was washed with brine, dried (Na$_2$SO$_4$) and concentrated under reduced pressure. The crude product was purified by silica gel column chromatography (30% EtOAc in hexane) to give 41 (270 mg, 87% over two steps) as a white solid.

$^1$H NMR (400 MHz, CDCl$_3$) δ: 8.22 (d, J=1.4 Hz, 1H), 7.92 (d, J=8.6 Hz, 1H), 7.79 (dd, J=8.6, 1.6 Hz, 1H), 6.77 (d, J=6.2 Hz, 2H), 6.64 (tt, J=9.2, 2.2 Hz, 1H), 4.74 (d, J=8.7 Hz, 1H), 4.05 (s, 1H), 3.84 (s, 1H), 3.71 (tt, J=9.4, 4.9 Hz, 1H), 3.14 (qd, J=15.1, 5.9 Hz, 2H), 3.01-2.84 (m, 4H), 2.81 (s, 3H), 1.94-1.79 (m, 1H), 1.34 (s, 9H), 0.87 (dd, J=10.4, 6.6 Hz, 6H).

$^{13}$C NMR (100 MHz, CDCl$_3$) δ: 173.5, 164.3 (d, J=12.7 Hz), 161.8 (d, J=13.2 Hz), 156.0 (d, J=7.8 Hz), 142.3 (t, J=8.9 Hz), 135.9, 133.9, 125.1, 121.8, 121.1, 112.6, 112.3, 108.8, 102.0 (t, J=25.4 Hz), 80.2, 73.0, 58.9, 54.7, 53.8, 35.2, 28.3, 27.3, 20.2, 20.0, 16.1.

Tert-butyl((2S,3R)-4-((2-(cyclopropylamino)-N-isobutylbenzo[d]thiazole)-6-sulfonamido)-1-(3,5-difluorophenyl)-3-hydroxybutan-2-yl)carbamate (42)

To a stirred solution of 41 (960 mg, 1.56 mmol) in dichloromethane (10 mL) was added mCPBA (807 mg, 4.68 mmol) at 0° C. under argon atmosphere and the mixture was stirred at 23° C. for 12 h. After this period, the reaction mixture was quenched by the addition of Saturated aqueous Na$_2$S$_2$O$_3$ (2 ml) and extracted with dichloromethane. The extracts were washed with Saturated aqueous NaHCO$_3$, dried (Na$_2$SO$_4$) and concentrated under reduced pressure. To the crude product in dry THF (10 mL) at 23° C. under argon atmosphere was added cyclopropylamine (0.35 mL, 4.68 mmol) and the mixture was stirred at 65° C. for 12 h. Solvent was removed under reduced pressure and the crude product was purified by silica gel column chromatography (50% EtOAc in hexane) to give 42 (880 mg, 91% over two steps) as a white solid.

$^1$H NMR (400 MHz, CDCl$_3$+CD$_3$OD) δ: 7.93 (s, 1H), 7.57-7.52 (m, 1H), 7.38 (d, J=8.5 Hz, 1H), 6.63 (d, J=6.6 Hz, 2H), 6.49 (t, J=9.0 Hz, 1H), 5.47 (d, J=9.4 Hz, 1H), 3.68-3.60 (m, 1H), 3.58-3.47 (m, 1H), 3.21-3.10 (m, 1H), 2.83 (dtd, J=39.5, 15.1, 13.3, 5.5 Hz, 4H), 2.61-2.50 (m, 2H), 1.84-1.71 (m, 1H), 1.18 (s, 9H), 0.75 (dd, J=9.7, 5.8 Hz, 8H), 0.62-0.57 (m, 2H).

$^{13}$C NMR (100 MHz, CDCl$_3$+CD$_3$OD) δ: 173.3, 164.1 (d, J=13.3 Hz), 161.7 (d, J=12.5 Hz), 156.7, 155.5, 131.0, 130.4, 125.4, 120.9, 118.3, 112.4 (d, J=24.1 Hz), 101.9 (d, J=26.8 Hz), 79.9, 72.8, 60.6, 58.6, 54.5, 53.5, 35.4, 28.2, 27.1, 26.6, 20.0, 14.1, 7.7.

N-((2R,3S)-3-Amino-4-(3,5-difluorophenyl)-2-hydroxybutyl)-2-(cyclopropylamino)-N-isobutylbenzo[d]thiazole-6-sulfonamide (43)

To a stirred solution of 42 (870 mg, 1.39 mmol) in dichloromethane (15 mL) was added TFA (5 mL) at 0° C. under argon atmosphere and the mixture was stirred at 23° C. for 1 h. Solvent was removed under reduced pressure to give 43 (730 mg, 100% yield).

Scheme 3: Synthesis of Inhibitors 13 and 14

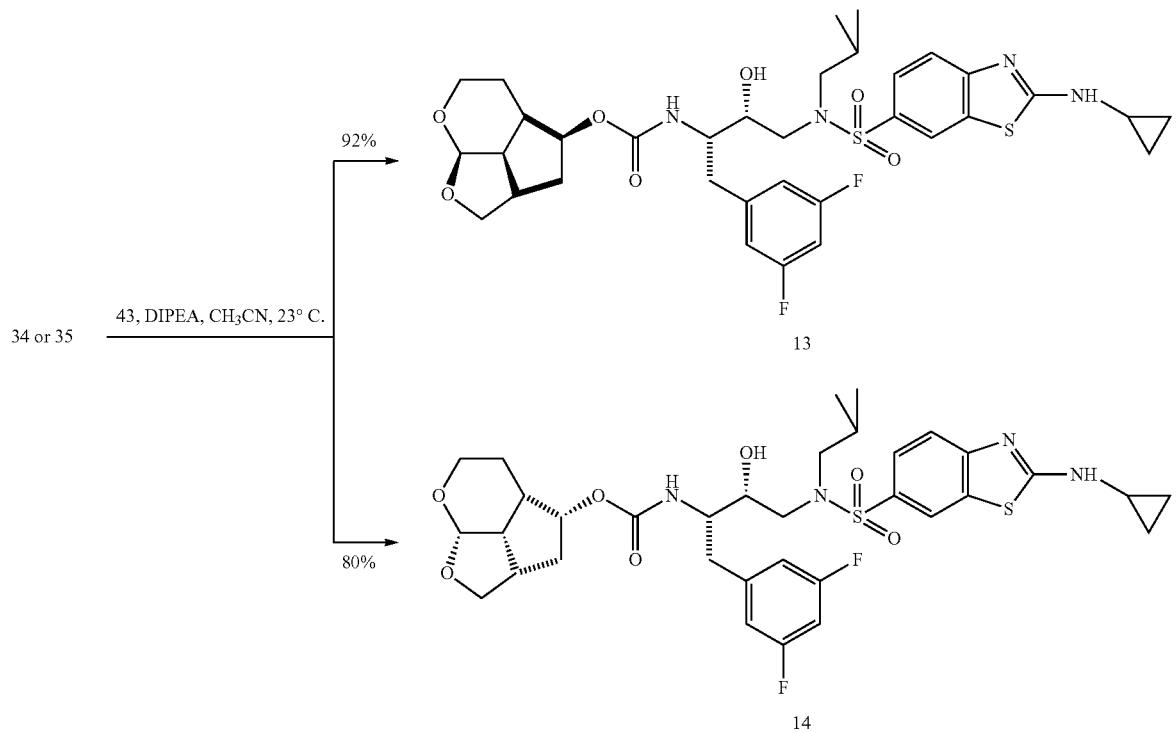

Experimental Procedure (2aR,2a¹R,4S,4aR,7aR)-Octahydro-2H-1,7-dioxacyclopenta[cd]inden-4-yl ((2S,3R)-4-((2-(cyclopropylamino)-N-isobutylbenzo[d]thiazole)-6-sulfonamido)-1-(3,5-difluorophenyl)-3-hydroxybutan-2-yl) carbamate (13)

To a stirred solution of activated alcohol 34 (6 mg, 0.018 mmol) and isoster 43 (11.3 mg, 0.021 mmol) in acetonitrile (2 mL) was added DIPEA (16 μL, 0.09 mmol) at 23° C. under argon atmosphere. The reaction mixture was stirred at 23° C. until completion. Upon completion, solvents were removed under reduced pressure and crude product was purified by silica gel column chromatography (65% EtOAc in hexane) to give 13 (12 mg, 92%).

¹H NMR (400 MHz, CDCl$_3$) δ: 8.10 (d, J=1.6 Hz, 1H), 7.70 (dd, J=8.5, 1.8 Hz, 1H), 7.57 (d, J=8.6 Hz, 1H), 6.92 (s, 1H), 6.78 (dd, J=16.1, 7.2 Hz, 2H), 6.68-6.61 (m, 1H), 5.21 (d, J=5.1 Hz, 1H), 5.13 (d, J=9.7 Hz, 1H), 4.99 (q, J=6.3 Hz, 1H), 3.94 (t, J=8.5 Hz, 2H), 3.89-3.79 (m, 3H), 3.64 (dt, J=9.0, 4.4 Hz, 1H), 3.34 (q, J=6.6, 6.2 Hz, 1H), 3.06 (dtd, J=33.4, 14.4, 13.4, 8.1 Hz, 4H), 2.89-2.82 (m, 1H), 2.77 (ddq, J=10.2, 6.8, 3.9 Hz, 2H), 2.68-2.60 (m, 1H), 2.52-2.39 (m, 2H), 2.07-1.97 (m, 1H), 1.85 (dt, J=13.7, 6.6 Hz, 1H), 1.62 (dt, J=13.1, 7.3 Hz, 1H), 1.38 (q, J=5.8 Hz, 2H), 0.93 (d, J=6.5 Hz, 4H), 0.89 (d, J=6.6 Hz, 4H), 0.80-0.77 (m, 2H).

¹³C NMR (100 MHz, CDCl$_3$) δ: 173.1, 164.3 (d, J=12.9 Hz), 161.8 (d, J=12.9 Hz), 156.1, 156.0, 142.3 (t, J=8.9 Hz), 131.6, 130.4, 125.5, 121.1, 118.9, 112.4 (d, J=18.7 Hz), 102.1, 100.7, 79.4, 73.1, 72.0, 60.1, 59.1, 54.9, 53.8, 41.9, 39.6, 36.0, 35.5, 29.9, 27.5, 26.9, 21.7, 20.3, 20.1, 8.2.

(2aS,2a¹S,4R,4aS,7aS)-Octahydro-2H-1,7-dioxacyclopenta[cd]inden-4-yl ((2S,3R)-4-((2-(cyclopropylamino)-N-isobutylbenzo[d]thiazole)-6-sulfonamido)-1-(3,5-difluorophenyl)-3-hydroxybutan-2-yl) carbamate (14)

The title inhibitor (14) was obtained by following the procedure outlined for inhibitor 13 (17 mg, 80% yield).

¹H NMR (400 MHz, CDCl$_3$) δ: 8.09 (s, 1H), 7.69 (dd, J=8.5, 1.8 Hz, 1H), 7.57 (d, J=8.5 Hz, 1H), 7.11 (s, 1H), 6.79 (d, J=6.2 Hz, 2H), 6.68-6.61 (m, 1H), 5.22 (t, J=7.4 Hz, 2H), 4.99 (q, J=6.0 Hz, 1H), 4.08 (s, 1H), 3.96-3.78 (m, 5H), 3.60 (dd, J=8.7, 5.6 Hz, 1H), 3.42-3.33 (m, 1H), 3.10 (dd, J=11.0, 4.9 Hz, 2H), 3.05 (d, J=3.8 Hz, 1H), 2.98 (dd, J=13.3, 8.3 Hz, 1H), 2.88 (t, J=6.6 Hz, 1H), 2.75 (dq, J=6.7, 3.4 Hz, 1H), 2.69-2.61 (m, 1H), 2.51-2.42 (m, 2H), 1.98 (dt, J=13.5, 6.8 Hz, 1H), 1.84 (dd, J=14.0, 6.9 Hz, 2H), 1.54 (dd, J=13.2, 6.6 Hz, 2H), 0.92 (d, J=6.5 Hz, 4H), 0.88 (d, J=6.6 Hz, 4H), 0.80-0.78 (m, 2H).

¹³C NMR (100 MHz, CDCl$_3$) δ: 173.1, 164.3 (d. J=13.0 Hz), 161.8 (d, J=13.0 Hz), 156.1 (d, J=31.9 Hz), 142.4 (t, J=8.7 Hz), 131.5, 130.5, 125.5, 121.1, 118.8, 112.5 (d, J=24.5 Hz), 102.3, 100.8, 79.6, 72.9, 71.9, 59.9, 59.1, 55.0, 53.8, 41.6, 39.8, 36.0 (d, J=7.5 Hz), 35.2, 29.8, 27.5, 26.8, 21.9, 20.3, 20.1, 8.1.

The present invention provides for the following embodiments, the numbering of which is not to be construed as designating levels of importance:

Embodiment 1 relates to a compound of the formula (I):

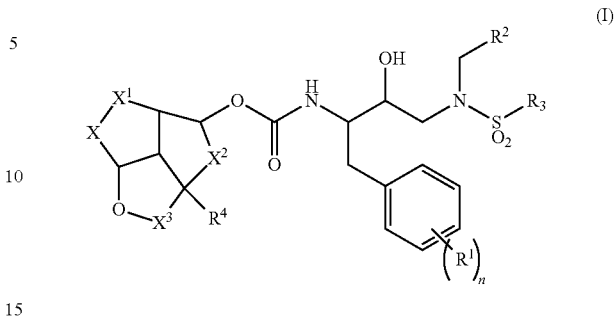

(I)

or a pharmaceutically acceptable salt, polymorph, prodrug, solvate or clathrate thereof, wherein: n is an integer from 0 to 3; X is (—CHR⁵—)$_m$ or —O—, wherein m is 1 or 2 and each R⁵ is, independently H, alkyl or alkoxy; X¹, X², and X³ are each, independently, (—CHR⁵—)$_m$; R¹ is alkyl, alkoxy, aryl, heterocyclyl, halo, hydroxy or amino; R² is alkyl; R³ is aryl, benzthiazole, benzoxazole, benzofuranyl or indolyl; and R⁴ is H, alkyl or alkoxy.

Embodiment 2 relates to the compound of Embodiment 1 wherein: X¹ is (—CHR⁵—)$_m$, wherein m is 2; X² is (—CHR⁵—)$_m$, wherein m is 1; X³ is (—CHR⁵—)$_m$, wherein m is 1; wherein each R⁵ is independently H, alkyl or alkoxy.

Embodiment 3 relates to the compound of Embodiment 1 wherein: X¹ is (—CHR⁵—)$_m$, wherein m is 1; X² is (—CHR⁵—)$_m$, wherein m is 1; X³ is (—CHR⁵—)$_m$, wherein m is 2; wherein each R⁵ is independently H, alkyl or alkoxy.

Embodiment 4 relates to the compound of Embodiments 1-3, wherein X is O.

Embodiment 5 relates to the compound of Embodiments 1-3, wherein X is (—CHR⁵—)$_m$, wherein m is 1 and R⁵ is H, alkyl or alkoxy.

Embodiment 6 relates to the compound of Embodiments 1-5, wherein R⁴ can be H or alkoxy.

Embodiment 7 relates to the compound of Embodiment 1, wherein the compound of the formula (I) is a compound of the formula:

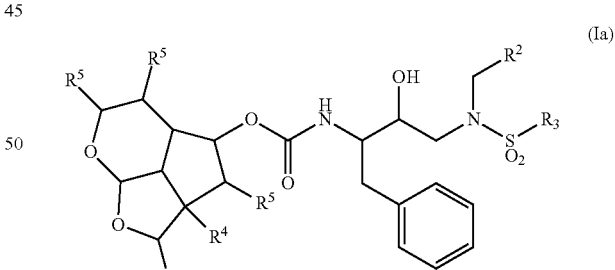

(Ia)

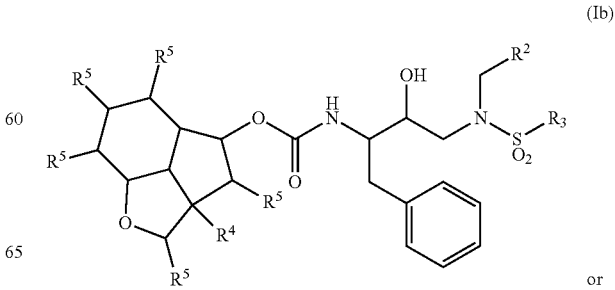

(Ib)

or (Ic)

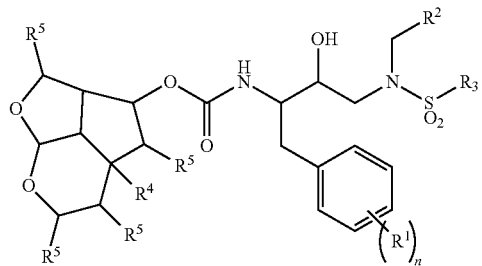

or a pharmaceutically acceptable salt, polymorph, prodrug, solvate or clathrate thereof, wherein n, $R^1$, $R^2$, $R^3$, and $R^4$ are as defined in Embodiment 1.

Embodiment 8 relates to the compound Embodiments 1-7, wherein n is 0.

Embodiment 9 relates to the compound of Embodiments 1-8, wherein $R^2$ is unsubstituted alkyl.

Embodiment 10 relates to the compound of Embodiments 1-8, wherein $R^3$ is aryl, benzthiazole or benzoxazole.

Embodiment 11 relates to the compound of Embodiments 10, wherein $R^3$ is phenyl.

Embodiment 12 relate to the compound of Embodiment 10, wherein $R^3$ is:

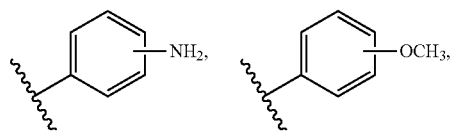

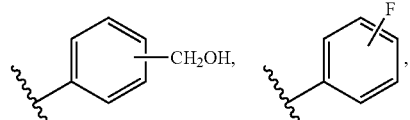

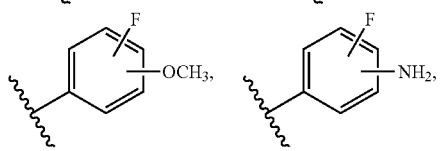

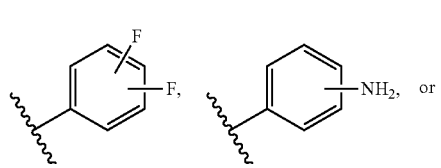

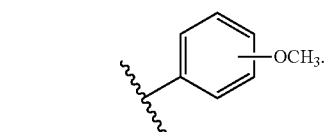

Embodiment 13 relates to the compound of Embodiment 12, wherein $R^3$ is:

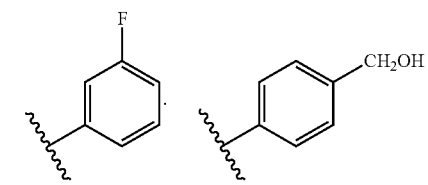

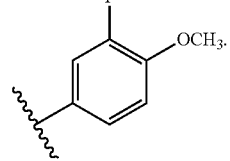

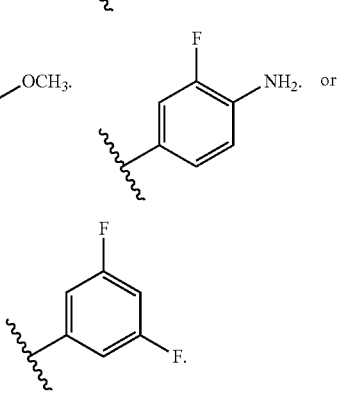

Embodiment 14 relates to the compound of Embodiment 10, wherein $R^3$ is:

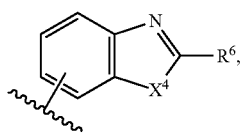

wherein $R^6$ is alkyl, alkylamino, cycloalkylamino, cycloalkyl heterocycloamino, heterocyclo cycloalkylamino or heterocycloamino; and $X^4$ is S, O or $NR^7$, wherein $R^7$ is H, alklyl, cycloalkyl or alkylaryl. $X^4$ can be S or O.

Embodiment 15 relates to the compound of Embodiment 1, wherein the compound is:

1

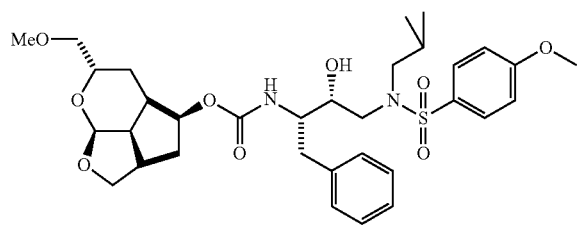

2

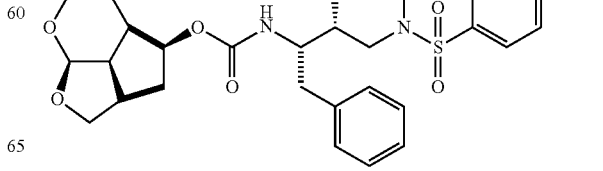

3
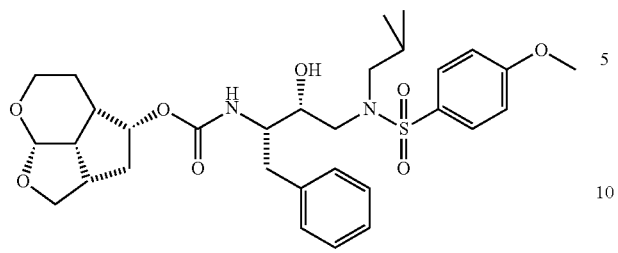
4
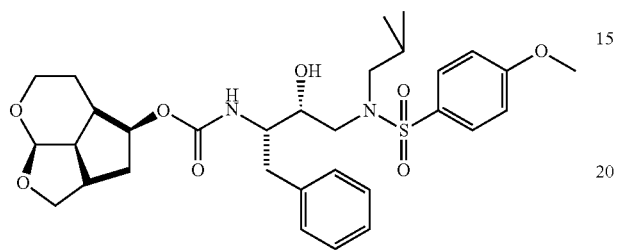
5
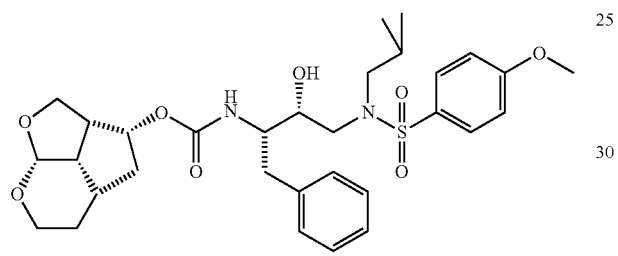
6
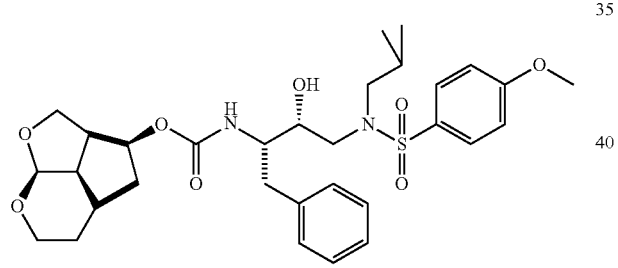
7
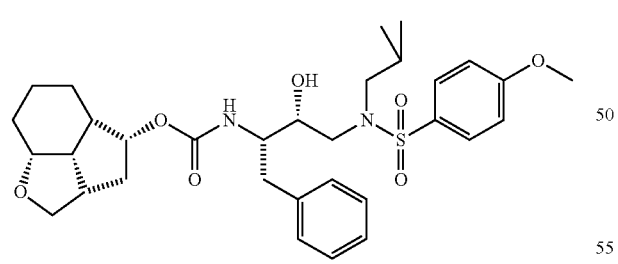
8
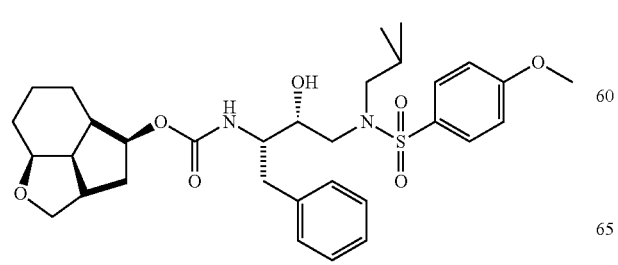
9
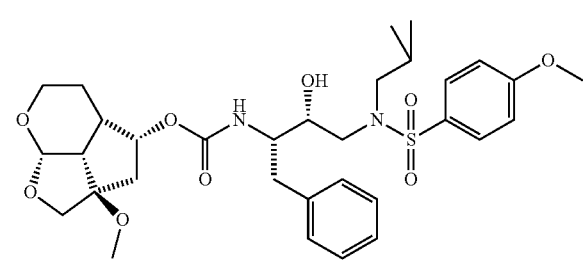
10
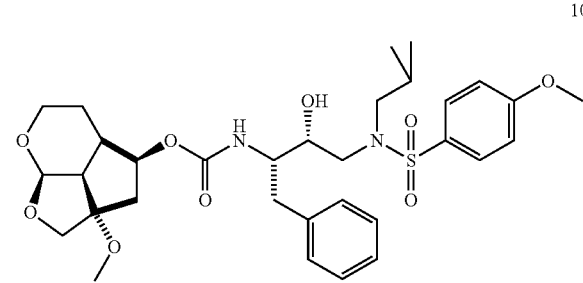
11
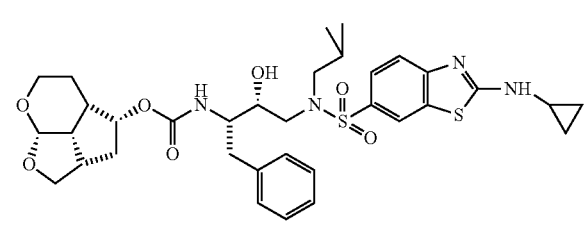
12
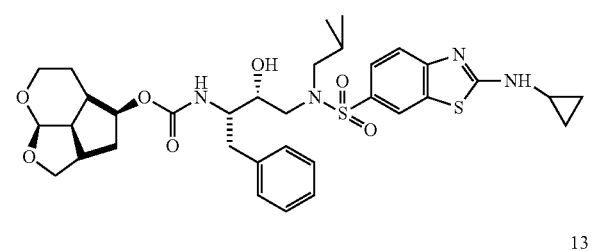
13
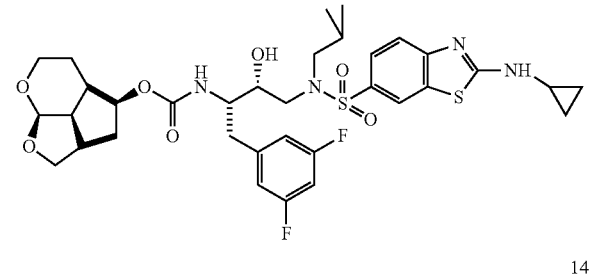
14
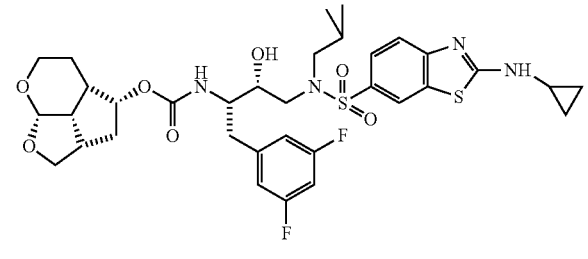

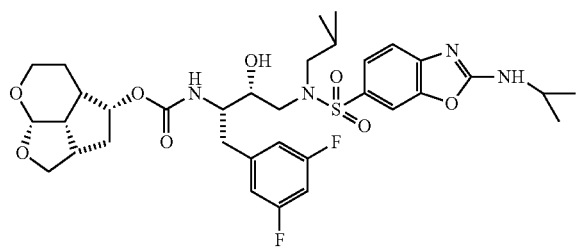
15
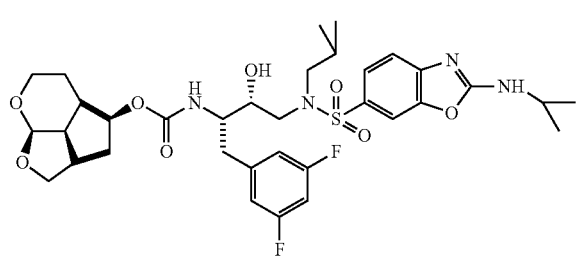
16
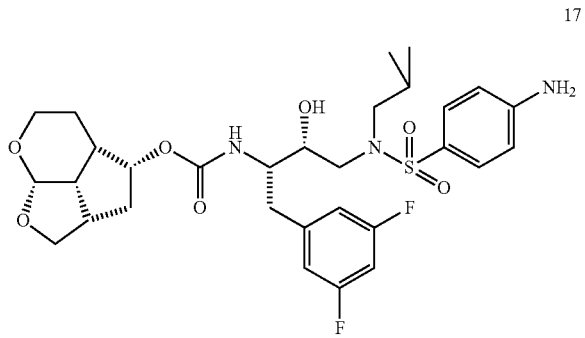
17
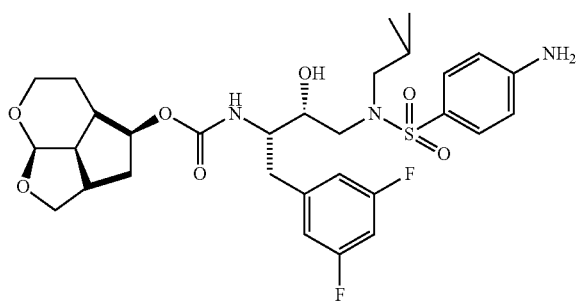
18
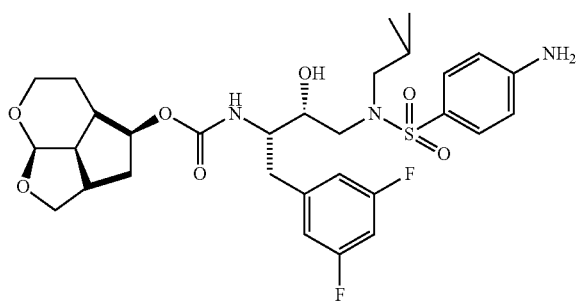
19
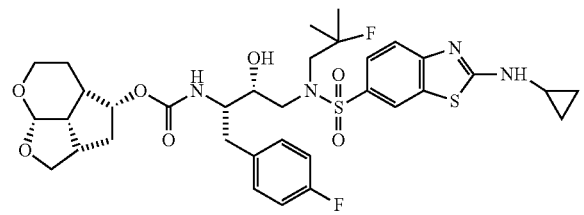
20
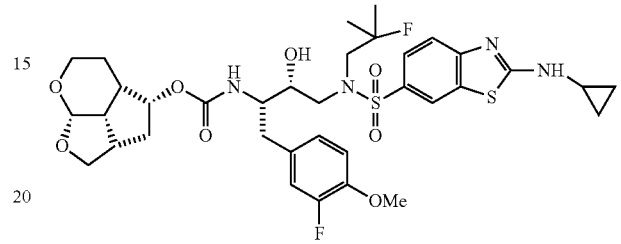
21
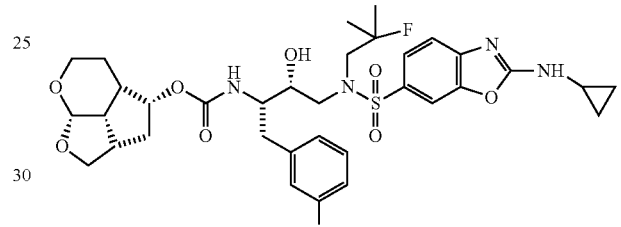
22
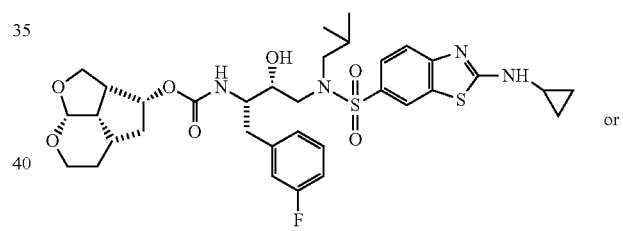
23
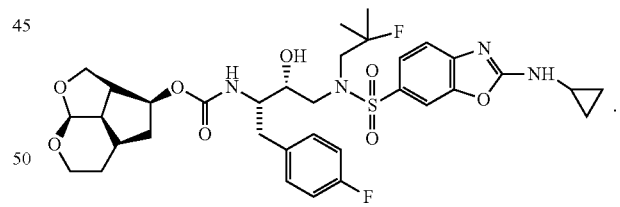
or
24
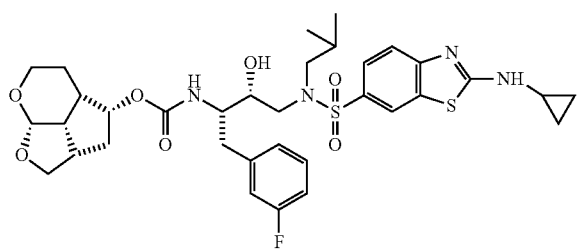
or a pharmaceutically acceptable salt, polymorph, prodrug, solvate or clathrate thereof.
Embodiment 16 relates to a compound of the formula (II):
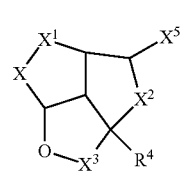
(II)

or a pharmaceutically acceptable salt, polymorph, prodrug, solvate or clathrate thereof, wherein: X, $X^1$—$X^3$, and $R^4$ are defined herein and wherein $X^5$ is selected from the group consisting of hydroxy, alkoxy, amino, C(O)R, C(O)OR, OC(O)OR, C(O)N(R)$_2$, OC(O)N(R)$_2$, C(S)N(R)$_2$, (CH$_2$)$_{0-2}$O(R)C(O)R, (CH$_2$)$_{0-2}$N(R)C(O)R, (CH$_2$)$_{0-2}$O(R)C(O)OR, (CH$_2$)$_{0-2}$O(R)C(O)OR or (CH$_2$)$_{0-2}$N(R)N(R)$_2$, wherein each R can be, independently, hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or two R groups bonded to a nitrogen atom or to adjacent nitrogen atoms can together with the nitrogen atom or atoms form a heterocyclyl.

Embodiment 17 relates to the compound of Embodiment 16 wherein: $X^1$ is (—CHR$^5$—)$_m$, wherein m is 2; $X^2$ is (—CHR$^5$—)$_m$, wherein m is 1; $X^3$ is (—CHR$^5$—)$_m$, wherein m is 1; wherein each $R^5$ is independently H, alkyl or alkoxy.

Embodiment 18 relates to the compound of claim 16 wherein: $X^1$ is (—CHR$^5$—)$_m$, wherein m is 1; $X^2$ is (—CHR$^5$—)$_m$, wherein m is 1; $X^3$ is (—CHR$^5$—)$_m$, wherein m is 2; wherein each $R^5$ is independently H, alkyl or alkoxy.

Embodiment 19 relates to the compound Embodiments 16-18, wherein X is O.

Embodiment 20 relates to the compound Embodiments 16-18, wherein X is (—CHR$^5$—)$_m$, wherein m is 1 and $R^5$ is H, alkyl or alkoxy.

Embodiment 21 relates to the compound Embodiments 16-20, wherein $R^4$ can be H or alkoxy. A pharmaceutical composition comprising a compound of claim 1 and one or more pharmaceutically acceptable excipients.

Embodiment 22 relates to a method for treating an HIV infection comprising administering a therapeutically effective amount of one or more compounds of claim 1 to a patient in need thereof.

Embodiment 23 relates to a compound of Embodiment 1 for use as a medicament for treating a patient in need of relief from an HIV infection.

What is claimed is:

1. A compound of the formula (I)

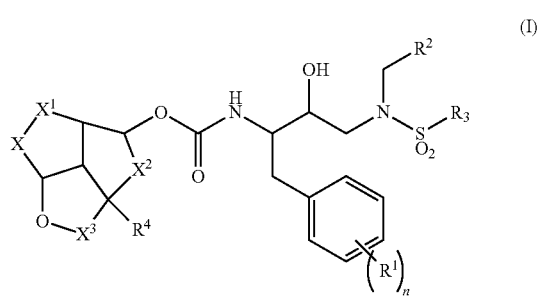

(I)

or a pharmaceutically acceptable salt, polymorph, or solvate thereof, wherein: n is an integer from 0 to 3; X is (—CHR$^5$—)$_m$ or —O—, wherein m is 1 or 2 and each $R^5$ is, independently H, alkyl or alkoxy;
$X^1$, $X^2$, and $X^3$ are each, independently, (—CHR$^5$—)$_m$;
$R^1$ is alkyl, alkoxy, aryl, heterocycyl, halo, hydroxy or amino;
$R^2$ is alkyl;
$R^3$ is aryl, benzthiazole, benzoxazole, benzofuranyl or indolyl; and
$R^4$ is H, alkyl or alkoxy.

2. The compound of claim 1, or a pharmaceutically acceptable salt, polymorph, or solvate thereof, wherein:

$X^1$ is (—CHR$^5$—)$_m$, wherein m is 2;
$X^2$ is (—CHR$^5$—)$_m$, wherein m is 1;
$X^3$ is (—CHR$^5$—)$_m$, wherein m is 1; and
wherein each $R^5$ is independently H, alkyl or alkoxy.

3. The compound of claim 1, or a pharmaceutically acceptable salt, polymorph, or solvate thereof, wherein:
$X^1$ is (—CHR$^5$—)$_m$, wherein m is 1;
$X^2$ is (—CHR$^5$—)$_m$, wherein m is 1;
$X^3$ is (—CHR$^5$—)$_m$, wherein m is 2; and
wherein each $R^5$ is independently H, alkyl or alkoxy.

4. The compound of claim 1, or a pharmaceutically acceptable salt, polymorph, or solvate thereof, wherein X is O.

5. The compound of claim 1, or a pharmaceutically acceptable salt, polymorph, or solvate thereof, wherein X is (—CHR$^5$—)$_m$, wherein m is 1 and $R^5$ is H, alkyl or alkoxy.

6. The compound of claim 1, or a pharmaceutically acceptable salt, polymorph, or solvate thereof, wherein $R^4$ can be H or alkoxy.

7. The compound of claim 1, or a pharmaceutically acceptable salt, polymorph, or solvate thereof, wherein the compound of the formula (I) is a compound of the formula:

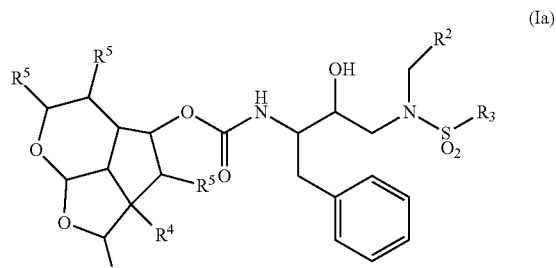

(Ia)

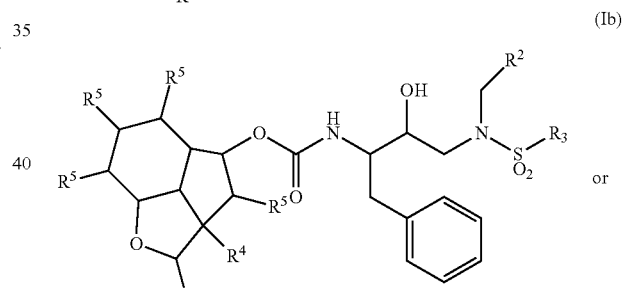

(Ib)

or

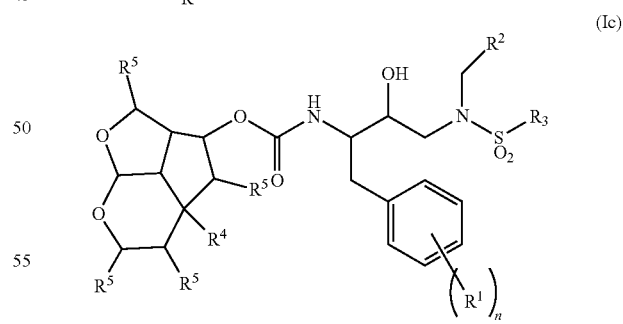

(Ic)

or a pharmaceutically acceptable salt, polymorph, prodrug, solvate or clathrate thereof, wherein n, $R^1$, $R^2$, $R^3$, and $R^4$ are as defined in claim 1.

8. The compound of claim 1, or a pharmaceutically acceptable salt, polymorph, or solvate thereof, wherein n is 0.

9. The compound of claim 1, or a pharmaceutically acceptable salt, polymorph, or solvate thereof, wherein $R^2$ is unsubstituted alkyl.

10. The compound of claim 1, or a pharmaceutically acceptable salt, polymorph, or solvate thereof, wherein $R^3$ is aryl, benzthiazole or benzoxazole.

11. The compound of claim 10, or a pharmaceutically acceptable salt, polymorph, or solvate thereof, wherein $R^3$ is phenyl.

12. The compound of claim 10, or a pharmaceutically acceptable salt, polymorph, or solvate thereof, wherein $R^3$ is:

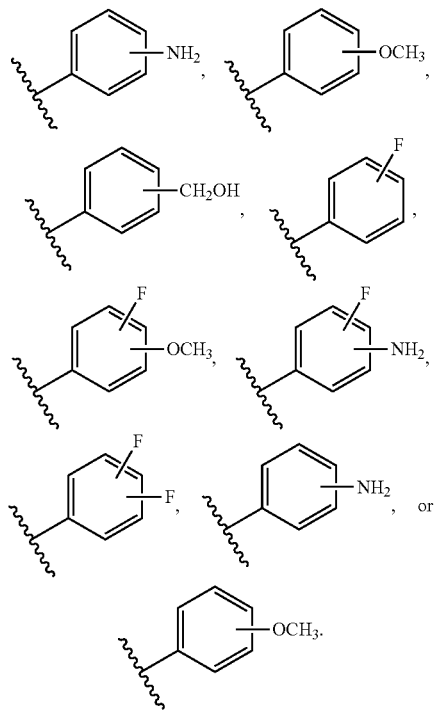

13. The compound of claim 12, or a pharmaceutically acceptable salt, polymorph, or solvate thereof, wherein $R^3$ is:

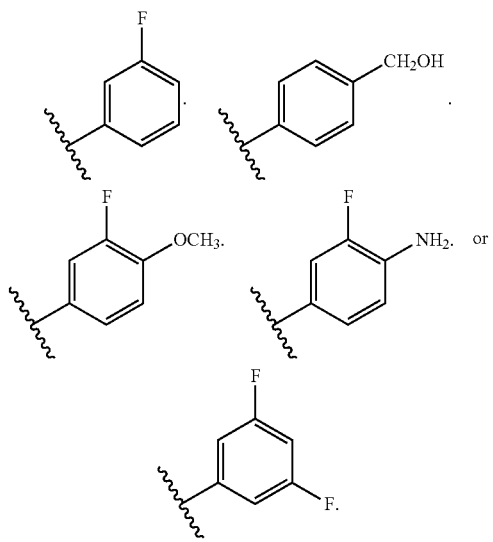

14. The compound of claim 10, or a pharmaceutically acceptable salt, polymorph, or solvate thereof, wherein $R^3$ is:

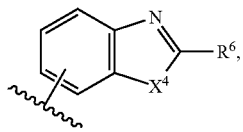

wherein $R^6$ is alkyl, alkylamino, cycloalkylamino, cycloalkyl heterocycloamino, heterocyclo cycloalkylamino or heterocycloamino; and $X^4$ is S, O or $NR^7$, wherein $R^7$ is H, alklyl, cycloalkyl or alkylaryl.

15. The compound of claim 1, wherein the compound is:

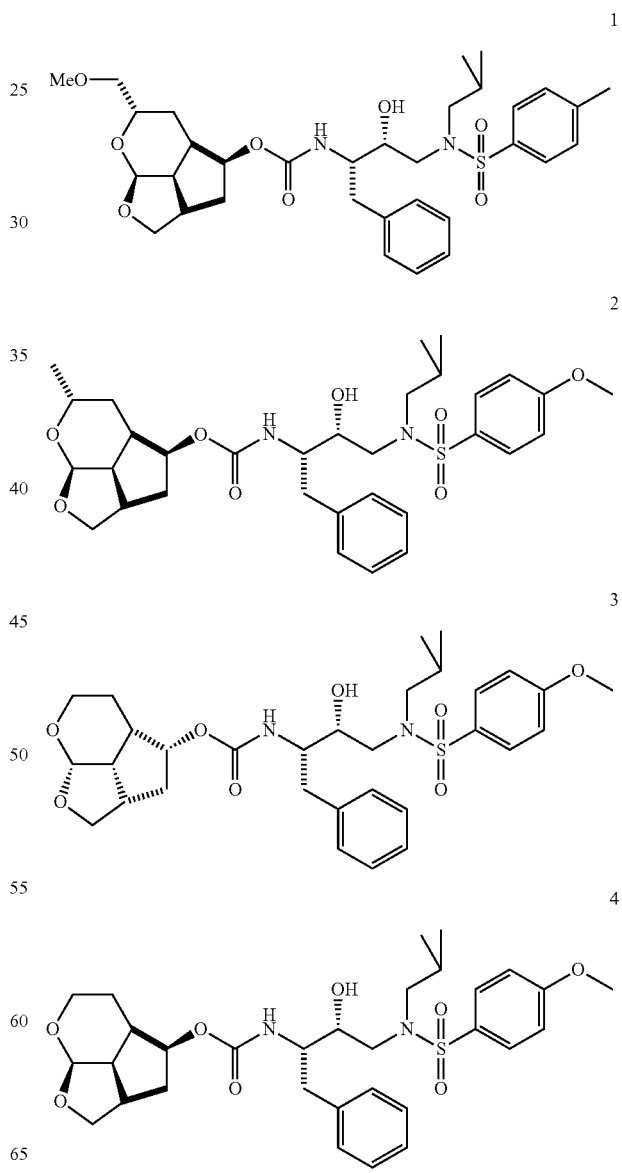

45
-continued
5
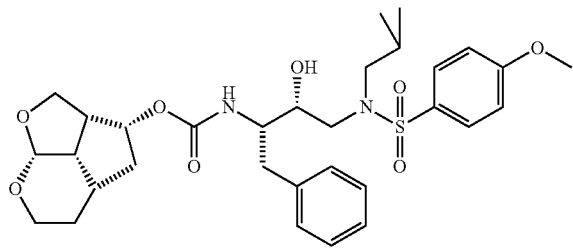
6
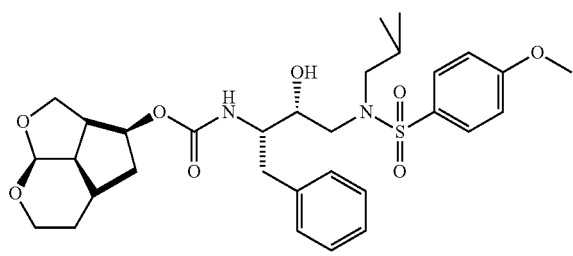
7
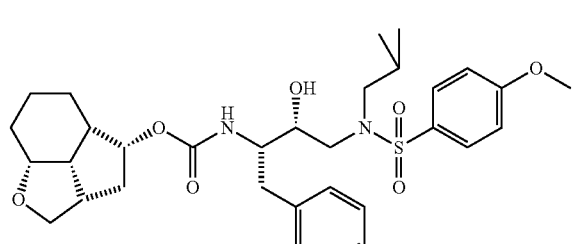
8
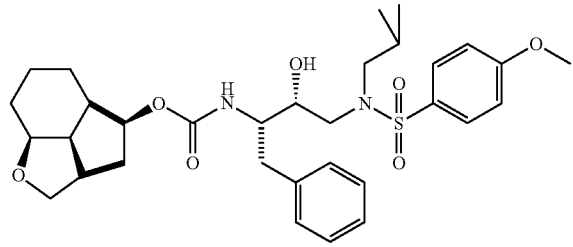
9
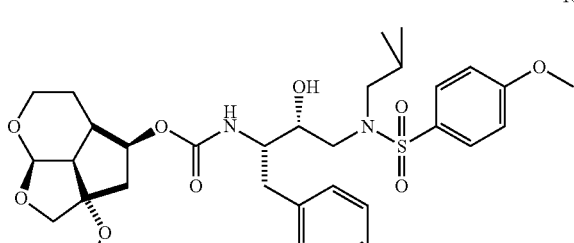
10
46
-continued
11
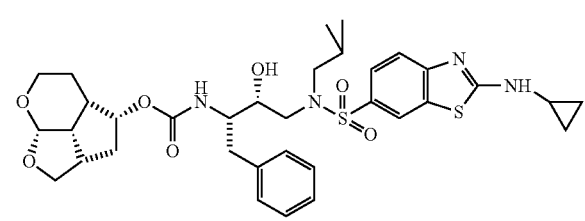
12
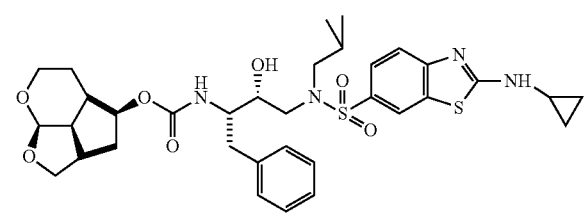
13
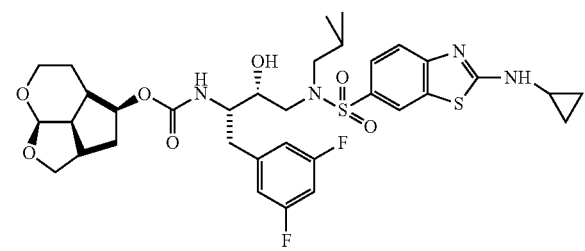
14
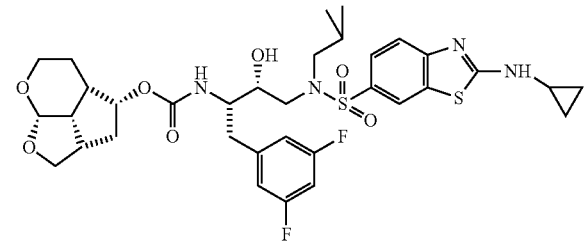
15
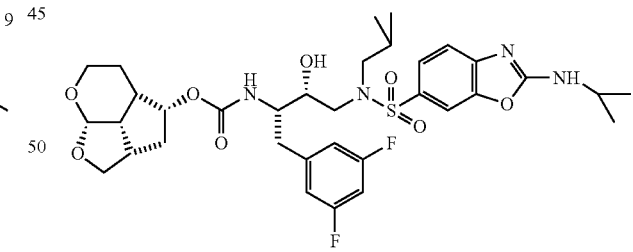
16
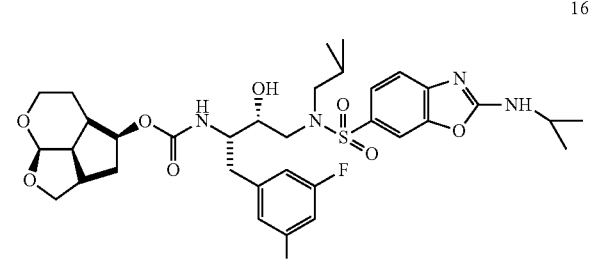

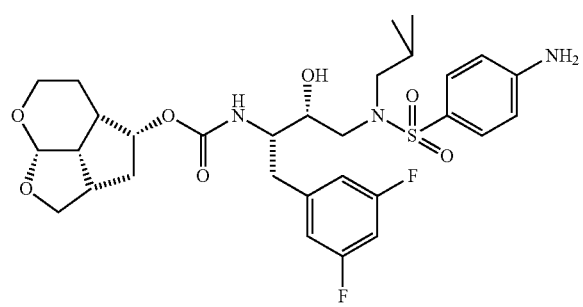
17
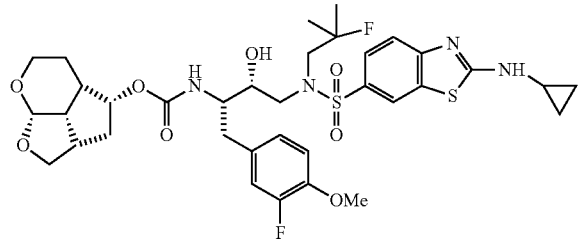
21
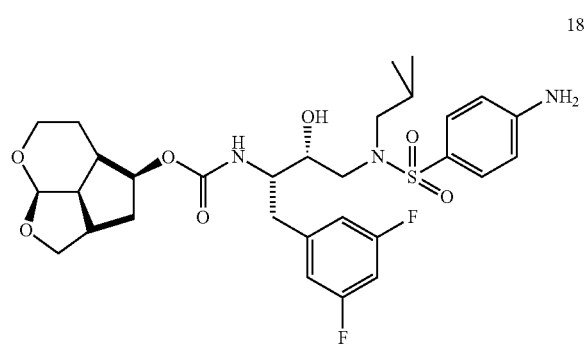
18
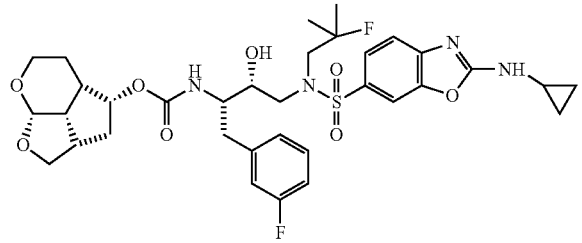
22
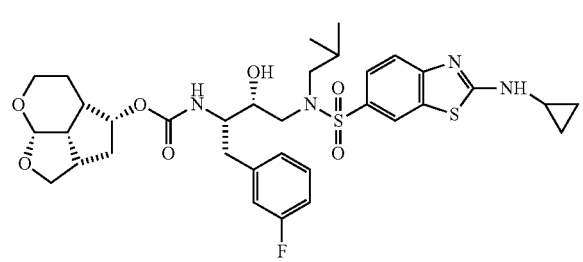
19
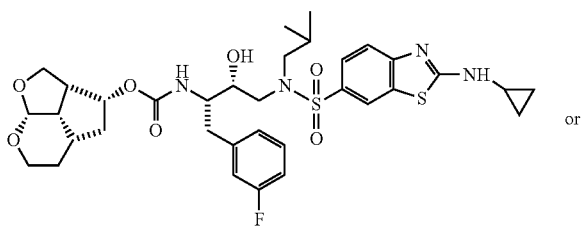
23
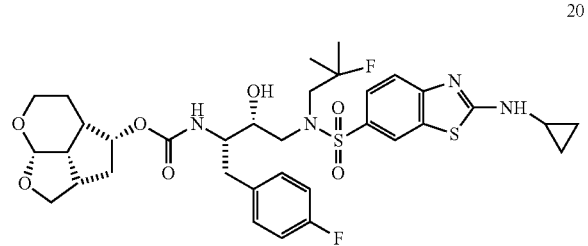
20
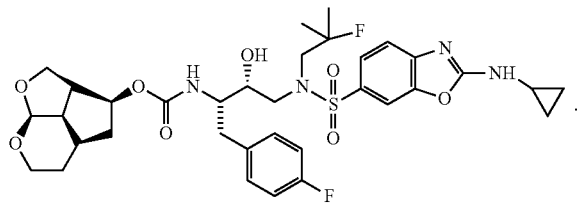
24
or a pharmaceutically acceptable salt, polymorph, or solvate thereof.
16. A pharmaceutical composition comprising a compound of claim 1, or a pharmaceutically acceptable salt, polymorph, or solvate thereof, and one or more pharmaceutically acceptable excipients.
* * * * *